United States Patent
Naidu et al.

(10) Patent No.: US 7,763,630 B2
(45) Date of Patent: Jul. 27, 2010

(54) HIV INTEGRASE INHIBITORS

(75) Inventors: B. Narasimhulu Naidu, Durham, CT (US); Margaret E. Sorenson, Meriden, CT (US); Manoj Patel, Berlin, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/132,145

(22) Filed: Jun. 3, 2008

(65) Prior Publication Data

US 2008/0306051 A1  Dec. 11, 2008

Related U.S. Application Data

(60) Provisional application No. 60/942,296, filed on Jun. 6, 2007.

(51) Int. Cl.
C07D 405/04 (2006.01)
C07D 405/14 (2006.01)
C07D 417/14 (2006.01)
A61K 31/513 (2006.01)

(52) U.S. Cl. ...................... 514/269; 544/319
(58) Field of Classification Search ................ 544/319; 514/269
See application file for complete search history.

(56) References Cited

U.S. PATENT DOCUMENTS

| | | | |
|---|---|---|---|
| 7,037,908 B2 | 5/2006 | Naidu et al. | |
| 7,115,601 B2 | 10/2006 | Naidu et al. | |
| 7,135,467 B2 | 11/2006 | Walker et al. | |
| 7,173,022 B2 | 2/2007 | Naidu et al. | |
| 7,176,196 B2 | 2/2007 | Naidu et al. | |
| 7,192,948 B2 | 3/2007 | Banville et al. | |
| 7,273,859 B2 | 9/2007 | Naidu | |
| 2005/0025774 A1 | 2/2005 | Crescenzi et al. | |
| 2005/0075356 A1 | 4/2005 | Di Francesco et al. | |
| 2006/0046985 A1 | 3/2006 | Crescenzi et al. | |
| 2007/0049606 A1 | 3/2007 | Banville et al. | |
| 2007/0111984 A1 | 5/2007 | Naidu et al. | |
| 2007/0111985 A1 | 5/2007 | Naidu et al. | |
| 2007/0112190 A1 | 5/2007 | Naidu | |
| 2007/0129379 A1 | 6/2007 | Naidu et al. | |
| 2007/0281917 A1 | 12/2007 | Naidu et al. | |
| 2008/0004265 A1 | 1/2008 | Walker et al. | |

FOREIGN PATENT DOCUMENTS

| | | |
|---|---|---|
| JP | 2004-244320 | 9/2004 |
| WO | WO 03/062211 | 7/2003 |
| WO | WO 2005/061490 | 7/2005 |
| WO | WO 2005/061501 | 7/2005 |
| WO | WO 2005/070901 | 8/2005 |
| WO | WO 2006/103399 | 10/2006 |
| WO | WO 2006/121831 | 11/2006 |
| WO | WO 2007/014352 | 2/2007 |
| WO | WO 2007/064619 | * 6/2007 |

OTHER PUBLICATIONS

Marcus et al., PubMed Abstract (Intervirology 45(4-6):260-6), 2002.*
van Heeswijk et al., PubMed Abstract (Antivir Ther. 6(4):201-29) Dec. 2001.*
Miles, PubMed Abstract (Community Pract. 78(8):292-4) Aug. 2005.*
U.S. Appl. No. 61/037,729, filed Mar. 19, 2008, Beaulieu et al.
Colarusso, S. et al., "Suzuki Coupling at the 2-Position of Densely Functionalized Pyrimidones", Synthesis, No. 8, pp. 1343-1350 (2006).
Pace, P. et al., "Dihydroxypyrimidine-4-carboxamides as Novel Potent and Selective HIV Integrase Inhibitors", J. Med. Chem., vol. 50, No. 9, pp. 2225-2239 (2007).
Petrocchi, A. et al., "From dihydroxypyrimidine carboxylic acids to carboxamide HIV-1 integrase inhibitors: SAR around the amide moiety", Bioorganic & Medicinal Chemistry Letters, vol. 17, pp. 350-353 (2007).
Summa, V. et al., "4,5-Dihydroxypyrimidine Carboxamides and N-Alkyl-5-hydroxypyrimidinone Carboxamides are Potent, Selective HIV Integrase Inhibitors with Good Pharmacokinetic Profiles in Preclinical Species", J. Med. Chem., vol. 49, No. 23, pp. 6646-6649 (2006).

* cited by examiner

Primary Examiner—Deepak Rao
(74) Attorney, Agent, or Firm—James Epperson

(57) ABSTRACT

The invention encompasses a series pyrimidinone compounds of Formula I which inhibit HIV integrase and prevent viral integration into human DNA. This action makes the compounds useful for treating HIV infection and AIDS. The invention also encompasses pharmaceutical compositions and methods for treating those infected with HIV.

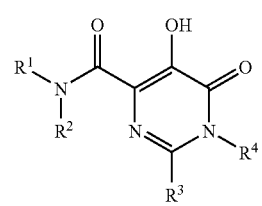

I

17 Claims, No Drawings

HIV INTEGRASE INHIBITORS

CROSS-REFERENCE TO RELATED APPLICATIONS

This application claims the benefit of U.S. Provisional Application Ser. No. 60/942,296 filed Jun. 6, 2007.

BACKGROUND OF THE INVENTION

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics (UNAIDS: Report on the Global HIV/AIDS Epidemic, December 1998), indicate that as many as 33 million people worldwide are infected with the virus. In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into four classes based on the viral protein they target and their mode of action. In particular, saquinavir, indinavir, ritonavir, nelfinavir atazanavir darunavir, amprenavir, fosamprenavir, lopinavir and tipranavir are competitive inhibitors of the aspartyl protease expressed by HIV. Zidovudine, didanosine, stavudine, lamivudine, zalcitabine, emtricitibine, tenofovir and abacavir are nucleoside reverse transcriptase inhibitors that behave as substrate mimics to halt viral cDNA synthesis. The non-nucleoside reverse transcriptase inhibitors, nevirapine, delavirdine, efavirenz and etravirine inhibit the synthesis of viral cDNA via a non-competitive (or uncompetitive) mechanism. Enfuvirtide and maraviroc inhibit the entry of the virus into the host cell. Used alone these drugs are effective in reducing viral replication. The effect is only temporary as the virus readily develops resistance to all known agents. However, combination therapy has proven very effective at both reducing virus and suppressing the emergence of resistance in a number of patients. In the US, where combination therapy is widely available, the number of HIV-related deaths has declined (Palella, F. J.; Delany, K. M.; Moorman, A. C.; Loveless, M. O.; Furher, J.; Satten, G. A.; Aschman, D. J.; Holmberg, S. D. *N. Engl. J. Med.* 1998, 338, 853-860).

Unfortunately, not all patients are responsive and a large number fail this therapy. In fact, approximately 30-50% of patients ultimately fail combination therapy. Treatment failure in most cases is caused by the emergence of viral resistance. Viral resistance in turn is caused by the rapid turnover of HIV-1 during the course of infection combined with a high viral mutation rate. Under these circumstances incomplete viral suppression caused by insufficient drug potency, poor compliance to the complicated drug regiment as well as intrinsic pharmacological barriers to exposure provides fertile ground for resistance to emerge. More disturbing are recent findings which suggest that low-level replication continues even when viral plasma levels have dropped below detectable levels (<50 copies/ml) (Carpenter, C. C.; Cooper, D. A.; Fischl, M. A.; Gatell, J. M.; Gazzard, B. G.; Hammer, S. M.; Hirsch, M. S.; Jacobsen, D. M.; Katzenstein, D. A.; Montaner, J. S.; Richman, D. D.; Saag, M. S.; Schechter, M.; Schooley, R. T.; Thompson, M. A.; Vella, S.; Yeni, P. G.; Volberding, P. A. *JAMA* 2000, 283, 381-390). Clearly, there is a need for new antiviral agents, preferably targeting other viral enzymes to reduce the rate of resistance and suppress viral replication even further.

HIV expresses three enzymes, reverse transcriptase, an aspartyl protease, and integrase. All three are targets for treating AIDS and HIV infection. HIV integrase is a component of the pre-integration complex of the virus that is assembled in the cell shortly after infection (Chiu, T. K.; Davies, D. R. *Curr. Top. Med. Chem.* 2004, 4, 965-977). This enzyme catalyzes the integration of proviral DNA into the host genome and is absolutely required for viral infectivity. Early experiments showed that mutating the active site of integrase within a proviral clone produces virus unable to replicate due to its inability to insert into the host chromosome (Englund, G.; Theodore, T. S.; Freed, E. O.; Engleman, A.; Martin, M. A. *J. Virol.* 1995, 69, 3216-3219). Selective HIV integrase inhibitors have been shown to possess effective anti-HIV activity in cell culture (Hazuda, D. J.; Felock, P.; Witmer, M.; Wolfe, A; Stillmock, K.; Grobler, J. A.; Espeseth, A.; Gabryelski, L.; Schleif, W.; Blau, C.; Miller, M. D. *Science,* 2000, 287, 646-650), and it is clear that this class of inhibitors is very effective as part of a combination regimen containing HIV inhibitors of different classes. An HIV integrase inhibitor, raltegravir (MK-0518, Isentress®), has been approved for use in treatment experienced patients based upon 48 week trial results (Cooper, D. A.; Gatell, J.; Rockstroh, J.; Katlama, C.; Yeni, P.; Lazzarin, A.; Xu, X.; Isaacs, R.; Teppler, H.; Nguyen, B. Y. 15*th Conference on Retroviruses and Opportunistic Infections*, Boston, Mass., Feb. 3-6, 2008 Abst. 105LB: Evering, T. H.; Markowitz, M. *Drugs Today,* 2007, 43, 865-877). In addition, a second integrase inhibitor, elvitegravir (GS-9137), completed a successful Phase II trial in combination with ritonavir boosting in naive and treatment experienced patients (Zolopa, A. 14*th Conference on Retroviruses and Opportunistic Infections*, Los Angeles, Calif. Feb. 25-28, 2007 Abst. 143LB). Thus, HIV-1 integrase is a promising target for novel anti-HIV-1 therapeutics.

DESCRIPTION OF THE INVENTION

The invention encompasses compounds of Formula I, including pharmaceutically acceptable salts, their pharmaceutical compositions, and their use in inhibiting HIV integrase and treating those infected with HIV or AIDS.

One aspect of the invention is compounds of Formula I

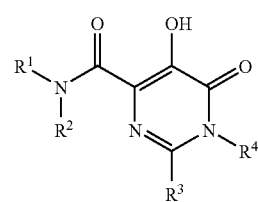

I wherein:
$R^1$ is $(Ar^1)$alkyl, $(Ar^1)(CON(R^{10})(R^{11}))$alkyl, $(Ar^1)(CO_2R^{16})$ alkyl, $(Ar^1)$hydroxyalkyl, or $(Ar^1)$oxyalkyl;
$R^2$ is hydrogen, alkyl, hydroxy, or alkoxy;
$R^3$ is $C(R^{17})(R^{18})(R^{19})$;
$R^4$ is alkyl;
$R^5$ is hydrogen, halo, hydroxy, cyano, alkyl, cycloalkyl, $C_{5-7}$cycloalkenyl, haloalkyl, alkoxy, alkylthio, haloalkoxy, $N(R^{10})(R^{11})$, $NHAr^2$, $N(R^8)SO_2R^9$, $N(R^8)COR^9$, $N(R^8)CO_2R^9$, $OCOR^9$, $OCO_2R^9$, $OCON(R^{10})(R^{11})$, OCH$_2$CO$_2$R$^9$, OCH$_2$CON(R$^{10}$)(R$^{11}$), COR$^8$, CO$_2$R$^8$, CON(R$^{10}$)(R$^{11}$), SOR$^9$, S(=N)R$^9$, SO$_2$R$^9$, SO$_2$N(R$^8$)(R$^8$), PO(OR$^8$)$_2$, C$_{2-4}$(R$^{14}$)alkynyl, R$^{15}$, Ar$^2$, or Ar$^3$;

R$^6$ is hydrogen, halo, hydroxy, cyano, alkyl, alkoxy, haloalkyl, haloalkoxy, or N(R$^8$)(R$^8$);

R$^7$ is hydrogen, halo, hydroxy, cyano, alkyl, alkoxy, haloalkyl, haloalkoxy, or N(R$^8$)(R$^8$);

R$^8$ is hydrogen, alkyl, or cycloalkyl;

R$^9$ is alkyl or cycloalkyl;

R$^{10}$ is hydrogen, alkyl, hydroxyalkyl, alkoxyalkyl or dialkylaminoalkyl;

R$^{11}$ is hydrogen, alkyl, hydroxyalkyl, alkoxyalkyl or dialkylaminoalkyl; or

N(R$^{10}$)(R$^{11}$) taken together is azetidinyl, pyrrolidinyl, (R$^{12}$)-piperidinyl, N—(R$^{13}$)-piperazinyl, morpholinyl, thiomorpholinyl, or dioxothiazinyl;

R$^{12}$ is hydrogen, alkyl, or hydroxyalkyl;

R$^{13}$ is hydrogen, alkyl, cyclolkyl, COR$^8$, or CO$_2$R$^8$;

R$^{14}$ is hydrogen, hydroxy, N(R$^8$)(R$^8$), SO$_2$R$^9$, OSO$_2$R$^9$, or dioxothiazinyl;

R$^{15}$ is azetidinonyl, pyrrolidinonyl, valerolactamyl, caprolactamyl, maleimido, oxazolidonyl, or dioxothiazinyl, and is substituted with 0-1 substituents selected from the group consisting of hydroxymethyl, acetoxymethyl, and aminomethyl;

R$^{16}$ is independently hydrogen or alkyl;

or two R$^{16}$'s taken together are CH$_2$CH$_2$, CH$_2$CH$_2$CH$_2$, CH$_2$CH$_2$CH$_2$CH$_2$, CH$_2$CH$_2$CH$_2$CH$_2$CH$_2$, CH$_2$CH$_2$CH$_2$CH$_2$CH$_2$CH$_2$, OCH$_2$CH$_2$, CH$_2$OCH$_2$, OCH$_2$CH$_2$CH$_2$, CH$_2$OCH$_2$CH$_2$, OCH$_2$CH$_2$CH$_2$, CH$_2$OCH$_2$CH$_2$CH$_2$, CH$_2$CH$_2$OCH$_2$CH$_2$, OCH$_2$CH$_2$CH$_2$CH$_2$CH$_2$, CH$_2$OCH$_2$CH$_2$CH$_2$CH$_2$, CH$_2$CH$_2$OCH$_2$CH$_2$CH$_2$, N(R$^8$)CH$_2$CH$_2$, CH$_2$N(R$^8$)CH$_2$, N(R$^8$)CH$_2$CH$_2$CH$_2$, CH$_2$N(R$^8$)CH$_2$CH$_2$, N(R$^8$)CH$_2$CH$_2$CH$_2$CH$_2$, CH$_2$N(R$^8$)CH$_2$CH$_2$CH$_2$, CH$_2$CH$_2$N(R$^8$)CH$_2$CH$_2$, N(R$^8$)CH$_2$CH$_2$CH$_2$CH$_2$CH$_2$, CH$_2$N(R$^8$)CH$_2$CH$_2$CH$_2$CH$_2$, or CH$_2$CH$_2$N(R$^8$)CH$_2$CH$_2$CH$_2$, provided that the two R$^{16}$'s are attached to a common carbon atom;

R$^{17}$ and R$^{18}$ taken together with the carbon to which they are attached is a 4-7-membered cyclic ether or a 4-7-membered cyclic thioether, and is substituted with 0-1 substituent selected from the group consisting of hydroxy, alkoxy, alkylthio, alkylSO, alkylSO$_2$, and alkyl;

R$^{19}$ is hydrogen, alkyl, hydroxyalkyl, alkylthioalkyl, alkoxy, alkoxyalkoxy, or alkylthioalkoxy;

Ar$^1$ is

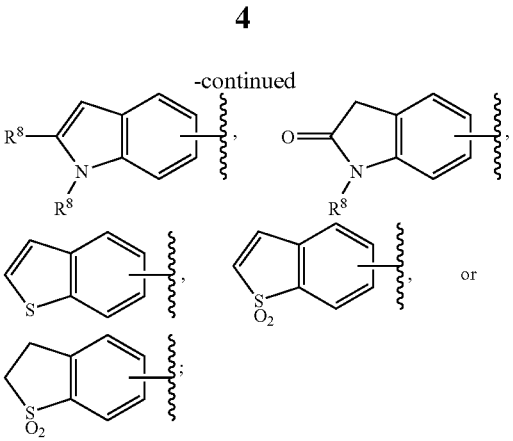

-continued

Ar$^2$ is tetrazolyl, triazolyl, oxadiazolyl, thiadiazolyl, pyrazolyl, imidazolyl, oxazolyl, thiazolyl, isoxazolyl, isothiazolyl, furanyl, thienyl, pyrrolyl, pyrimidinyl, pyrazinyl, pyridinyl, hydroxypyridinyl, quinolinyl, isoquinolinyl, or indolyl, and is substituted with 0-2 substituents selected from the group consisting of halo, cyano, benzyl, alkyl, alkoxy, N(R$^{10}$)(R$^{11}$), CON(R$^{10}$)(R$^{11}$), CO$_2$R$^8$, CONHSO$_2$N(R$^8$)(R$^8$), CONHSO$_2$N(R$^8$)(phenyl), and CONHSO$_2$N(R$^8$)(halophenyl); and Ar$^3$ is phenyl substituted with 0-2 substituents selected from the group consisting of halo, cyano, hydroxy, alkyl, alkoxy, alkoxymethyl, haloalkyl, haloalkoxy, N(R$^{10}$)(R$^{11}$), CON(R$^8$)(R$^8$), and CH$_2$N(R$^{10}$)(R$^{11}$), or is dioxolanylphenyl;

or a pharmaceutically acceptable salt thereof.

Another aspect of the invention is a compound of Formula I where R$^1$ is (Ar$^1$)alkyl.

Another aspect of the invention is a compound of Formula I where R$^1$ is

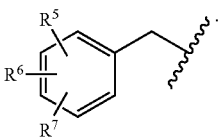

Another aspect of the invention is a compound of Formula I where R$^1$ is

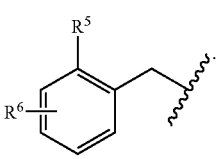

Another aspect of the invention is a compound of Formula I where R$^1$ is

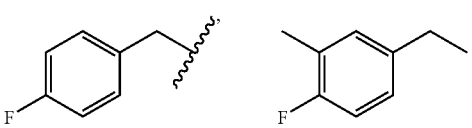

-continued

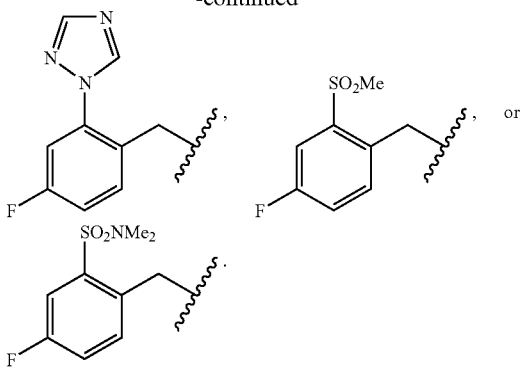

Another aspect of the invention is a compound of Formula I where $R^2$ is hydrogen.

Another aspect of the invention is a compound of Formula I where $R^3$ is,

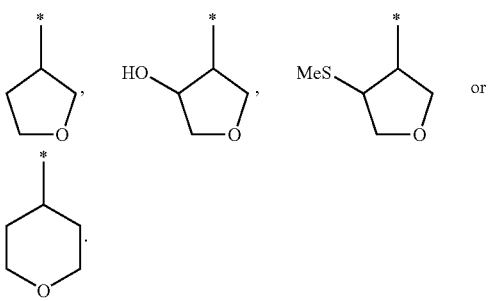

Another aspect of the invention is a compound of Formula I where $R^4$ is methyl.

Another aspect of the invention is a compound of Formula I where $R^5$ is $R^{15}$.

Another aspect of the invention is a compound of Formula I where $R^5$ is $Ar^2$.

Another aspect of the invention is a compound of Formula I where $R^{19}$ is hydrogen.

For a compound of Formula I, any scope of a variable, including $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $Ar^1$, $Ar^2$, and $Ar^3$, can be used independently with the scope of any other instance of a variable.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. "Haloalkyl" and "haloalkoxy" include all halogenated isomers from monohalo to perhalo. Terms with a hydrocarbon moiety (e.g. alkoxy) include straight and branched isomers for the hydrocarbon portion. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R.

A "4-7-membered cyclic ether" means a cyclic alkyl ring system where one atom is oxygen. One example is tetrahydrofuranyl.

A "4-7-membered cyclic thioether" means a cyclic alkyl ring system where one atom is sulfur. One example is tetrahydrothiophene. "$(Ar^1)$oxyalkyl" means $Ar^1$ is attached at the oxygen.

"Dioxolanyphenyl" means

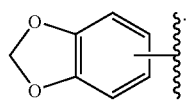

"Dioxothiazinyl" means

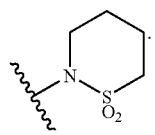

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. An example of enantiomers is shown below. Methods of making and separating stereoisomers are known in the art.

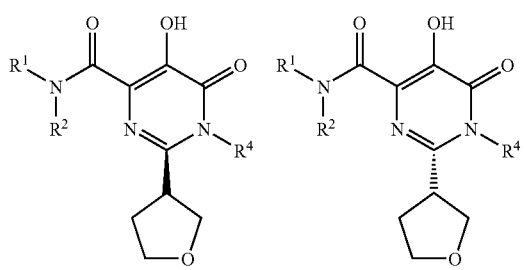

The invention includes all tautomeric forms of the compounds. An example of a tautomeric pair is shown below.

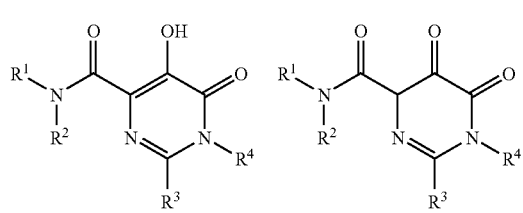

Synthetic Methods

General methods useful for the synthesis of the compounds of this invention are shown below. Related compounds can be made by reactions known to those skilled in the art.

Synthetic methods for the preparation of pyrimidines similar to those described in the current invention have been published (Gardelli, C. et al PCT Appl. WO 02/06246). The compounds of the present invention can be synthesized according to Scheme I. In Scheme I, aryl nitrile I-1 can be reacted with N-hydroxylamine I-2. The intermediate I-3 generated from this reaction can be isolated but more often is reacted in one pot with dialkyl acetylenedicaboxylate I-4 and can yield the diesters I-5a or I-5b. The diesters I-5a or I-5b can be converted to pyrimidine carboxylate I-6 by heating at or above 120° C. in an appropriate solvent. The ester I-6 can be condensed with amine I-7 to give the amide I-8. The amide coupling reaction can be carried out under a variety of conditions such as those disclosed in Jerry March, Advanced Organic Chemistry, $3^{rd}$ edition, John Wiley & Sons, 1985.

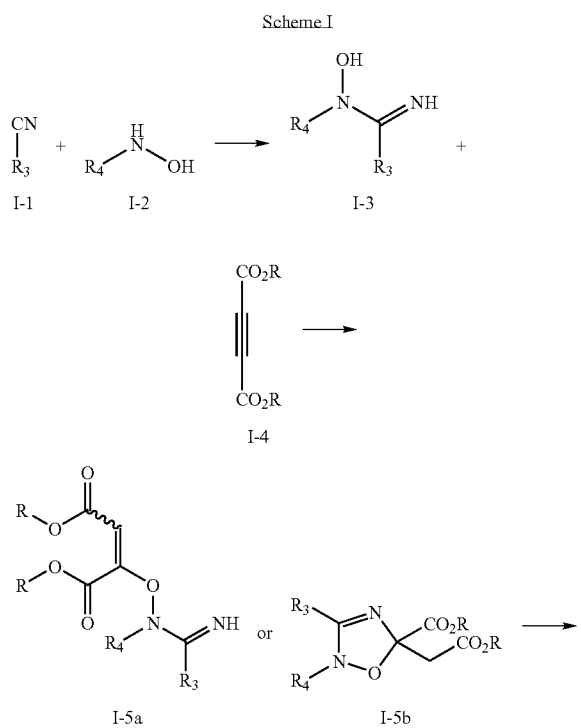

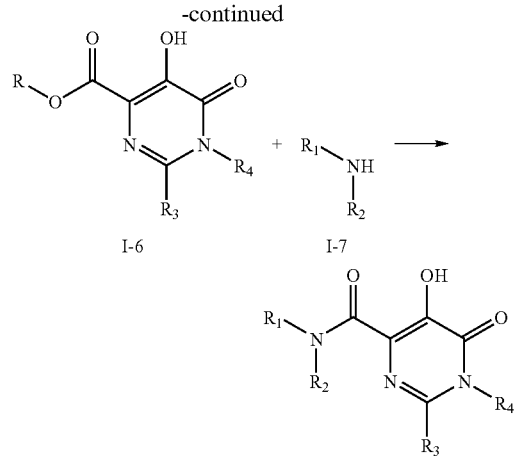

In Scheme II, an alternative pathway is shown in which the $R^6$ group is introduced at a later stage of the synthesis. Synthetic methods for the preparation of pyrimidines similar to those described in the current invention have been published (Sunderland, J. S.; et al. Inorg. Chem. (2001), 40, 6756-6756). Some of the compounds can be synthesized according to Scheme II. In Scheme II, an oxalic acid diester II-1 can be condensed with glycolate II-2 using sodium hydride or a similar base. The intermediate II-3 generated from this reaction can be isolated but more often is reacted in one pot with an appropriately substituted amidine II-4 and can yield the pyrimidinone heterocycle II-5. Intermediate II-5 can be coupled with amine II-6. Alternatively, the pyrimidinone II-5 can be alkylated with a suitable electrophile under basic conditions. Then intermediate II-9 can be coupled with amine II-6. The amides, II-8 and II-10 can then be treated under conditions appropriate for cleaving the protecting group P. For alkyl groups, where P is alkyl, this can be accomplished by $BBr_3$ or other conditions known in the art. Alternatively, when P is a benzylic or substituted benzylic group the ether can be cleaved under reductive conditions, oxidative conditions or acidic conditions. Protecting groups, R and P, useful for the synthesis of compounds such as 1-9 can be found in Greene, T. W. and Wutz, P. G. M. Protective Groups in Organic Synthesis, Second Edition, 1991, John Wiley and Sons, New York.

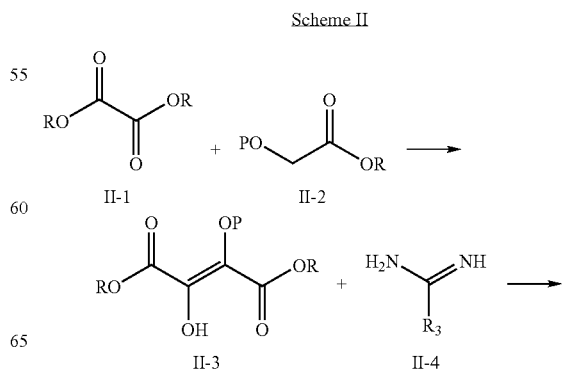

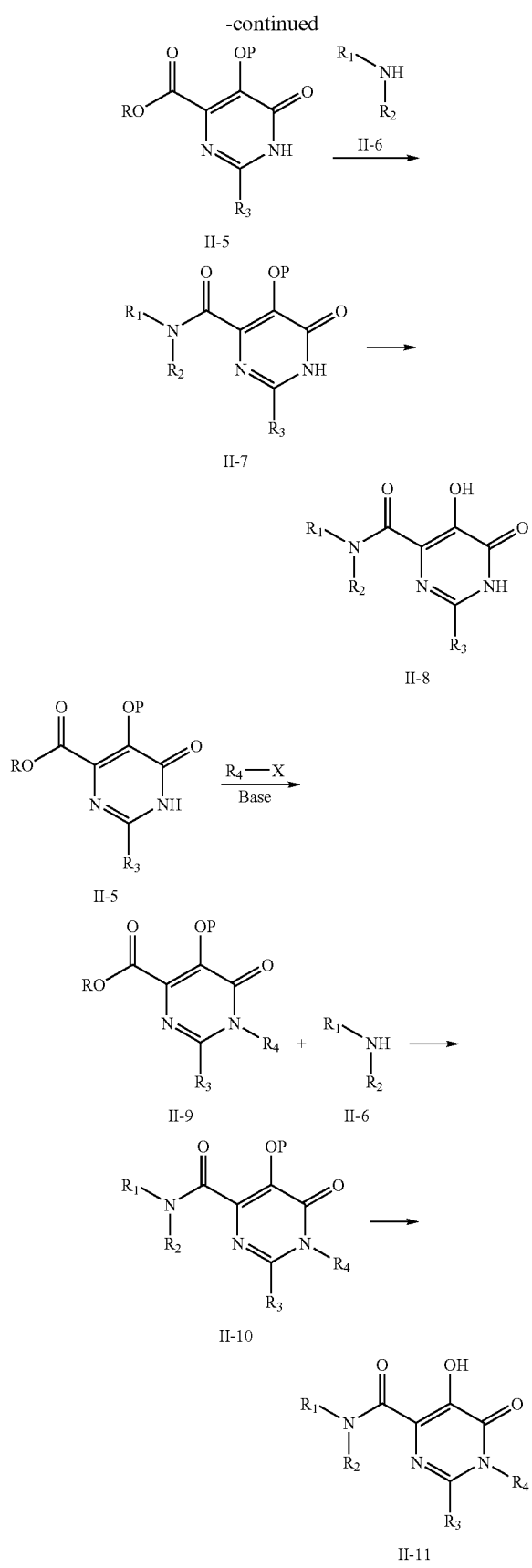

Biological Methods

HIV-Integrase Inhibition Activity. To evaluate in-vitro activity against HIV-integrase, 5 pmole of biotin labeled substrate DNA was bound to 100 μg of Streptavidin coated PVT SPA beads (Amersham Pharmacia Biotech). Recombinant integrase (0.26 ng) was incubated with the beads for 90 min at 37° C. Unbound enzyme was removed by washing the complex followed by addition of inhibitors and 0.1 fmol of P33 labeled target DNA. The reaction was stopped by adding EDTA to a final concentration of 10 mM. Samples were counted in TopCountNXT (Packard) and the CPM was used as a measure of integration. The reaction condition was as described in A. Engelman and R. Craigie, *J. Virol.* 69, 5908-5911 (1995). The sequences of substrate and target DNA were described in *Nucleic Acid Research* 22, 1121-1122 (1994). Results are shown in the Table 1. Activity equal to A refers to a compound having $IC_{50}$=0.002 to 0.10 μM while B and C denote compounds having $IC_{50}$=0.1 to 1.0 μM and $IC_{50} \geq 1.0$ μM respectively.

Compound A

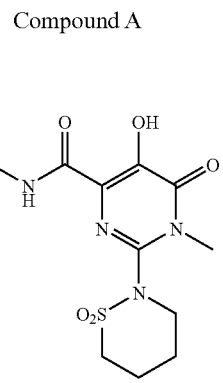

HIV-Integrase binding assay. In this assay competitive binding experiments with test compounds and a radiolabeled integrase inhibitor (compound A) are performed against purified integrase. SPA bead/DNA/enzyme complexes were prepared as for the integrase inhibition assay except, to each well, 0.69 μl of integrase enzyme (0.42 mg/μl) was used per 2 μl of LTR DNA-attached scintillation proximity beads (stock 50 mg/ml). Binding reactions were carried out in 96-well white polystyrene assay plates (Corning, #3600). The following was added sequentially to each well: 20 μl of water or 20 μl of human serum (Cellgro Cat #35-060-CL), 5 μl of serially diluted compound (in 50% DMSO/50% integrase SPA buffer), 5 μl of [$^3$H]-compound I (6,000 cpm/μl in SPA buffer) and 20 μl of bead/DNA/enzyme complex. The plates were shaken for 2 hours and then allowed to sit at room temperature without shaking overnight. The [$^3$H]-compound I binding was measured using a Topcount scintillation counter. Cheng and Prusoff equations were used to convert the inhibition of compound 1 binding into the corresponding Ki value. Results are shown in the Table 1. Activity equal to A refers to a compound having Ki=0.001 to 0.003 μM while B and C denote compounds having Ki=0.003 to 0.05 μM and Ki$\geq$0.050 μM respectively.

Inhibition of HIV replication. A recombinant NL-Rluc virus was constructed in which a section of the nef gene from NL4-3 was replaced with the *Renilla* Luciferase gene. The NL-RLuc virus was prepared by co-transfection of two plasmids, pNLRLuc and pVSVenv. The pNLRLuc contains the NL-Rluc DNA cloned into pUC18 at the PvuII site, while the pVSVenv contains the gene for VSV G protein linked to an LTR promoter. Transfections were performed at a 1:3 ratio of pNLRLuc to pVSVenv on 293T cells using the LipofectAMINE PLUS kit from Invitrogen (Carlsbad, Calif.) according to manufactures instruction, and the pseudotype virus generated was titered in MT-2 cells.

Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/drug\ conc.)^m]$ (Johnson V A, Byington R T. Infectivity Assay. In *Techniques in HIV Research*. ed. Aldovini A, Walker B D. 71-76. New York: Stockton Press. 1990). The anti-viral activity of compounds was evaluated under three serum conditions, 10% FBS, 15 mg/ml human serum albumin/10% FBS or 40% human serum/5% FBS, and the results from at least 2 experiments were used to calculate the $EC_{50}$ values. Results are shown in the Table 2. Activity equal to A refers to a compound having $EC_{50}$=0.003 to 0.10 μM while B and C denote compounds with $EC_{50}$=0.1 to 1.0 μM and $EC_{50} \geq 1.0$ μM respectively.

TABLE 1

| Example | Inhibition Activity | Binding Activity | Antiviral Activity |
|---|---|---|---|
| 1 | A | | A |
| 2 | A | | A |
| 3 | | A | A |
| 4 | | B | A |
| 5 | | B | A |
| 6 | | B | A |
| 7 | | B | A |
| 8 | | B | A |
| 9 | | A | A |
| 10 | | B | A |
| 11 | | A | A |
| 12 | | A | A |
| 13 | | A | A |
| 14 | | A | A |
| 15 | A | | A |
| 16 | A | | A |
| 17 | A | | A |
| 18 | | B | A |
| 19 | | B | A |
| 20 | | B | A |
| 21 | | A | A |
| 22 | | B | A |
| 23 | | B | A |
| 24 | | B | A |
| 25 | | B | A |
| 26 | | A | A |

Pharmaceutical Composition and Methods of Use

The compounds of this invention inhibit HIV integrase. HIV integrase inhibitors belonging to a class of diketo acid compounds prevented viral integration and inhibited HIV-1 replication in cells (Hazuda et al. *Science* 2000, 287, 646). Recently, HIV integrase inhibitors have been approved by the FDA for treating AIDS and HIV infection.

Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable salt thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100, or a pharmaceutically acceptable salt thereof.

Another aspect of the invention is a method wherein the agent is an HIV budding or maturation inhibitor.

Another aspect of the invention is a method wherein the budding or maturation inhibitor is PA-457, or a pharmaceutically acceptable salt thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100 or a pharmaceutically acceptable salt thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt thereof.

Another aspect of the invention is the composition wherein the agent is an HIV integrase inhibitor.

"Combination," "coadministration," "concurrent," and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Table 2 lists some agents useful in treating AIDS and HIV infection which are suitable for this invention.

TABLE 2

| DRUG NAME | MANUFACTURER | INDICATION |
|---|---|---|
| ANTIVIRALS | | |
| 097 (non-nucleoside reverse transcriptase inhibitor) | Hoechst/Bayer | HIV infection, AIDS, ARC |
| Amprenavir 141 W94 GW 141 (protease inhibitor) | Glaxo Wellcome | HIV infection, AIDS, ARC |
| Abacavir (1592U89) GW 1592 (RT inhibitor) | Glaxo Wellcome | HIV infection, AIDS, ARC |
| Acemannan | Carrington Labs (Irving, TX) | ARC |

TABLE 2-continued

| DRUG NAME | MANUFACTURER | INDICATION |
|---|---|---|
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection, ARC, PGL HIV positive, AIDS |
| AL-721 | Ethigen (Los Angeles, CA) | |
| Alpha Interferon HIV in combination w/Retrovir | Glaxo Wellcome | Kaposi's sarcoma |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) (protease inhibitor) | Bristol-Myers Squibb/ Novartis | HIV infection, AIDS, ARC |
| BMS-234475 (CGP-61755) (protease inhibitor) | Bristol-Myers Squibb/ Novartis | HIV infection, AIDS, ARC |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral, CMV retinitis |
| Delaviridine (RT inhibitor) | Pharmacia-Upjohn | HIV infection, AIDS, ARC |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 (protease inhibitor) | AVID (Camden, NJ) | HIV infection, AIDS, ARC |
| Efavirenz (DMP 266) (−)6-Chloro-4-(S)-cyclopropylethynyl-4(S)-trifluoro-methyl-1,4-dihydro-2H-3,1-benzoxazin-2-one, STOCRINE (non-nucleoside RT inhibitor) | DuPont Merck | HIV infection, AIDS, ARC |
| EL10 | Elan Corp, PLC (Gainesville, GA) | HIV infection |
| Famciclovir | Smith Kline | herpes zoster, herpes simplex |
| FTC (reverse transcriptase inhibitor) | Emory University | HIV infection, AIDS, ARC |
| GS 840 (reverse transcriptase inhibitor) | Gilead | HIV infection, AIDS, ARC |
| HBY097 (non-nucleoside reverse transcriptase inhibitor) | Hoechst Marion Roussel | HIV infection, AIDS, ARC |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-associated diseases |
| Lamivudine, 3TC (reverse transcriptase inhibitor) | Glaxo Wellcome | HIV infection, AIDS, ARC, also with AZT |
| Lobucavir | Bristol-Myers Squibb | CMV infection |
| Nelfinavir (protease inhibitor) | Agouron Pharmaceuticals | HIV infection, AIDS, ARC |
| Nevirapine (RT inhibitor) | Boeheringer Ingleheim | HIV infection, AIDS, ARC |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 (protease inhibitor) | Pharmacia Upjohn | HIV infection, AIDS, ARC |
| Probucol | Vyrex | HIV infection, AIDS |
| RBC-CD4 | Sheffield Med. Tech (Houston, TX) | HIV infection, AIDS, ARC |
| Ritonavir (protease inhibitor) | Abbott | HIV infection, AIDS, ARC |
| Saquinavir (protease inhibitor) | Hoffmann-LaRoche | HIV infection, AIDS, ARC |
| Stavudine; d4T Didehydrodeoxy-thymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV-positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) (reverse transcriptase inhibitor) | Gilead | HIV infection, AIDS |
| Combivir ® (reverse transcriptase inhibitor) | GSK | HIV infection, AIDS |
| abacavir succinate (or Ziagen ®) (reverse transcriptase inhibitor) | GSK | HIV infection, AIDS |
| Reyataz ® (atazanavir) | Bristol-Myers Squibb | HIV infection, AIDS |
| Fuzeon (Enfuvirtide, T-20) | Roche/Trimeris | HIV infection, AIDS, viral fusion inhibitor |
| Trizivir ® | | HIV infection, AIDS |
| Kaletra ® | Abbott | HIV infection, AIDS ARC |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |

TABLE 2-continued

| DRUG NAME | MANUFACTURER | INDICATION |
|---|---|---|
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide Granulocyte Colony Stimulating Factor | Ciba-Geigy Corp. Amgen | Kaposi's sarcoma AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche in combination w/AZT | Kaposi's sarcoma, AIDS, ARC |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

DESCRIPTION OF SPECIFIC EMBODIMENTS

Intermediate 1

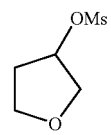

Tetrahydrofuran-3-yl methanesulfonate. To a stirred ice-cold solution of alcohol (25 g, 284 mmol), Et$_3$N (47.5 mL, 341 mmol) and DMAP (1.22 g, 10 mmol) in THF (500 mL) was added drop wise MsCl (24.2 mL, 312.4 mmol) over 10 min. The resulting white slurry was stirred for 5 h while allowing to a warm to room temperature. Then, filtered through a plug of celite and filter cake was washed with THF (200 mL). The combined filtrate was concentrated and the resulting yellow liquid was distilled under reduced pressure to afford product as a colorless liquid (37.3 g, 79%, bp: 100-110° C./0.3 mm Hg). $^1$H NMR (500 MHz, CDCl$_3$) δ: 5.32-5.29 (1H, m), 4.02-3.85 (4H, m), 3.03 (3H, s), 2.25-2.20 (2H, m).

Intermediate 2

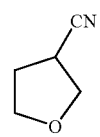

Tetrahydrofuran-3-carbonitrile. A mixture of NaCN (21.81 g, 445 mmol), Bu$_4$NCN (5 g) and mesylate (37 g, 222.6 mmol) in anhydrous CH$_3$CN was at 80° C. for 16 h. Then, the reaction mixture was cooled to room temperature, diluted with water (250 mL) and extracted with CH$_2$Cl$_2$ (3×100 mL). The combined organic layers were dried (Na$_2$SO$_4$), filtered and concentrated to give dark brown liquid. Distillation under vaccuo afforded product as a colorless liquid (17.62 g, 82%, bp: 59-63° C./3 mm Hg). $^1$H NMR (500 MHz, CDCl$_3$) δ: 4.02 (1H, t, J=8.2 Hz), 3.96-3.84 (3H, m), 3.10-3.04 (1H, m), 2.33-2.19 (2H, m).

Intermediate 3

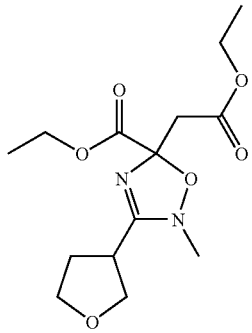

Ethyl 5-(2-ethoxy-2-oxoethyl)-2-methyl-3-(tetrahydrofuran-3-yl)-2,5-dihydro-1,2,4-oxadiazole-5-carboxylate. To stirred mixture of nitrile (9.712 g, 100 mmol) and N-methylhydroxylamine hydrochloride (19.44 g, 125 mmol) in ethanol/water (1:1, 100 mL) was added Na$_2$CO$_3$ (6.9 g, 65 mmol). After 21 h, the reaction mixture was concentrated and resulting white residue was re-dissolved in ethanol/water (1:1, 100 mL). To this was added diethyl acetylenedicarboxylate (17 mL, 116 mmol) over 10 min. After 30 min, the reaction mixture was diluted with brine (100 mL) and extracted with CH$_2$Cl$_2$ (4×100 mL). The combined organic phases dried (MgSO$_4$), filtered and concentrated to afford orange oil. Flash chromatography on silica gel column using Hex/EtOAc mixtures (7:3 to 1:1) furnished product as a yellow oil (27.66 g, 88%). $^1$H NMR (500 MHz, CDCl$_3$) δ: 4.31-4.17 (2H, m), 4.13 (2H, q, J=7.2 Hz), 4.04 (1H, td, J=7.9, 1.2 Hz),3.94-3.89 (1H, m),3.88-3.82 (2H, m), 3.26 (1H, dd, J=16.5, 4.6 Hz), 3.12 (3H, s), 2.98-2.89 (2H, m), 2.23-2.17 (2H, m), 1.29 (3H, td, J=7.2, 3.4 Hz), 1.23 (3H, td, J=7.0, 1.2 Hz). HRMS (M+H) calcd for C$_{14}$H$_{23}$N$_2$O$_6$: 3151556; found: 315.1548.

Intermediate 4

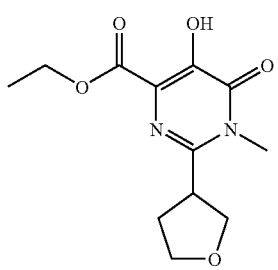

Ethyl 5-hydroxy-1-methyl-6-oxo-2-(tetrahydrofuran-3-yl)-1,6-dihydropyrimidine-4-carboxylate. A solution of oxadiazoline (20.85 g, 66.34 mmol) in xylenes (200 mL) was stirred at reflux for 38 h. The resulting dark reaction was concentrated and purified on silica gel column using mixture of 30-100% EtOAc/Hex followed by mixture of 5-25% MeOH/CH$_2$Cl$_2$ to afford product as a white solid 9.4008 g, 53%). $^1$H NMR (500 MHz, CDCl$_3$) δ: 10.53 (1H, s), 4.48-4.38 (2H, m), 4.16-4.08 (2H, m), 4.4 (1H, dd, J=14.2, 8.1 Hz), 3.94 (1H, dd, J=14.0, 8.2 Hz), 3.60 (3H, s), 3.53-3.47 (1H, m), 2.40-2.25 (2H, m), 1.42 (3H, td, J=7.2, 0.9 Hz). HRMS (M+H) calcd for C$_{12}$H$_{17}$N$_2$O$_5$: 269.1137; found: 269.1131.

Example 1

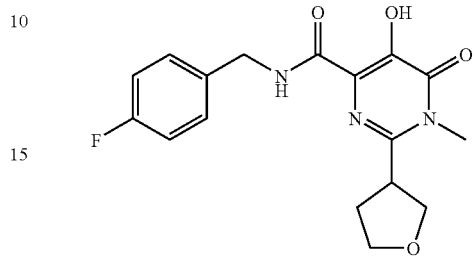

N-(4-Fluorobenzyl)-5-hydroxy-1-methyl-6-oxo-2-(tetrahydrofuran-3-yl)-1,6-dihydropyrimidine-4-carboxamide. A mixture of intermediate 4 (3.226 g, 12.025 mmol), 4-fluorobenzylamine (3.76 g, 30.5 mmol) and Et$_3$N (2.2 mL, 15.63 mmol) in DMF/EtOH (1:1, 25 mL) was heated at 90° C. for 8 h. Then, the reaction mixture was cooled, diluted with 1N HCl (50 mL) and extracted with EtOAc (3×50 mL). The combined organic layers dried (Na$_{2S}$O$_4$/carbon) filtered and concentrated to give brown oil. This material was purified on C18 column using 30-70% MeOH/H$_2$O containing trace amount of NH4OAc to provide product which was crystallized from MeOH/H$_2$0 (2.1797 g, 52%). $^1$H NMR (500 MHz, CDCl$_3$) δ: 12.00 (1H, s), 7.80 (1H, br s), 7.33-7.29 (2H, m), 7.05 (2H, t, J=8.5 Hz), 4.62-4.54 (2H, m), 4.12-4.06 (2H, m), 3.99-3.89 (2H, m), 3.61 (3H, s), 3.54-3.48 (1H, m), 2.37-2.30 (1H, m), 2.22-2.15 (1H, m). HRMS (M+H) calcd for C$_{17}$H$_{19}$FN$_3$O$_4$: 348.1360; found: 348.1367. Anal calcd for C$_{17}$H$_{18}$FN$_3$O$_4$: C, 58.78; H, 5.33; N, 12.09; F, 5.47 found: C, 58.89; H, 4.97; N, 12.10; F, 5.34.

The following Examples were prepared according to the procedure for Example 1 using appropriate benzylamine (some benzylamines used here were prepared using general procedures reported by Naidu, B. N. et al in U.S. Pat. No. 7,557,447) and intermediate 4 in DMF/EtOH or EtOH as reaction solvent.

Example 2

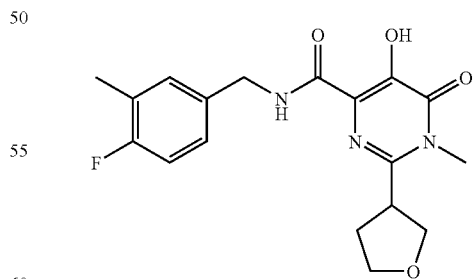

N-(4-Fluoro-3-methylbenzyl)-5-hydroxy-1-methyl-6-oxo-2-(tetrahydrofuran-3-yl)-1,6-dihydropyrimidine-4-carboxamide. $^1$H NMR (500 MHz, CDCl$_3$) δ: 12.03 (1H, s), 7.80-7.76 (1H, m), 7.18-7.08 (2H, m), 6.97 (1H, t, J=8.9 Hz), 4.57-4.49 (2H, m), 4.12-4.06 (2H, m), 3.98-3.89 (2H, m), 3.60 (3H, s), 3.54-3.48 (1H, m), 2.36-2.29 (1H, m)m2.27 (3H, Example 3

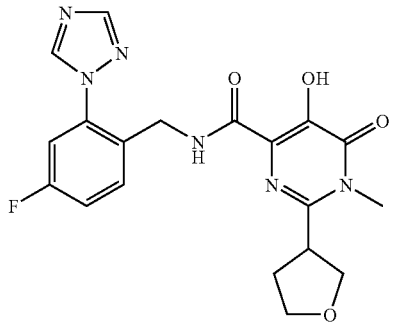

N-(4-fluoro-2-(1H-1,2,4-triazol-1-yl)benzyl)-5-hydroxy-1-methyl-6-oxo-2-(tetrahydrofuran-3-yl)-1,6-dihydropyrimidine-4-carboxamide. White solid (55% yield). $^1$H NMR (500 MHz, CDCl$_3$) δ: 11.96 (s, 1H), 8.97 (brs, 1H), 8.45 (s, 1H), 8.26 (s, 1H), 7.70 (dd, 1H, J=8.55,6.1 Hz), 7.21-7.23 (m, 1H), 7.10 (dd, 1H, J=8.39, 2.59 Hz), 4.46-4.51 (m, 1H), 4.37-4.41 (m, 1H), 4.21-4.24 (m, 1H), 4.13 (t, 1H, J=8.09 Hz), 4.01-4.04 (m, 1H), 3.93-3.97 (m, 1H), 3.59 (s, 3H), 3.48-3.55 (m, 2H). LCMS (M+H)+=415.35. Anal calcd for C$_{21}$H$_{27}$FN$_4$O$_6$S 0.5 H$_2$O: C, 55.87; H, 5.36; N, 18.62; found: C, 56.18; H, 5.77; N, 18.27.

Example 4

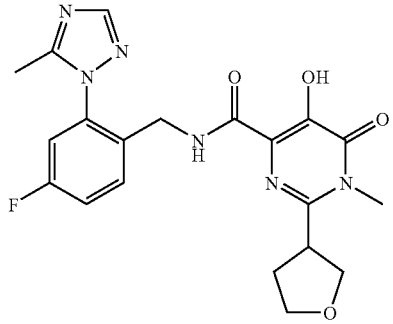

N-(4-fluoro-2-(5-methyl-1H-1,2,4-triazol-1-yl)benzyl)-5-hydroxy-1-methyl-6-oxo-2-(tetrahydrofuran-3-yl)-1,6-dihydropyrimidine-4-carboxamide. White solid (50% yield). $^1$H NMR (500 MHz, CDCl$_3$) δ: 12.03 (brs, 1H), 8.57 (brs, 1H), 8.19 (s, 1H), 7.69 (dd, 1H, J=8.55,5.8 Hz), 7.25-7.29 (m, 1H), 7.02 (dd, 1H, J=8.24, 2.44 Hz), 4.35-4.39 (m, 1H), 4.21-4.26 (m, 2H), 4.12 (t, 1H, J=7.93 Hz), 3.92-4.02 (m, 1H), 3.60 (s, 3H), 3.51-3.55 (m, 1H), 2.53 (s, 3H), 2.32-2.37 (m, 1H), 2.22-2.26 (m, 1H). LCMS (M+H)+=429.38. Anal calcd for C$_{21}$H$_{27}$FN$_4$O$_6$S 0.5 H$_2$O: C, 55.87; H, 5.36; N, 18.62; found: C, 56.18; H, 5.77; N, 18.27.

Example 5

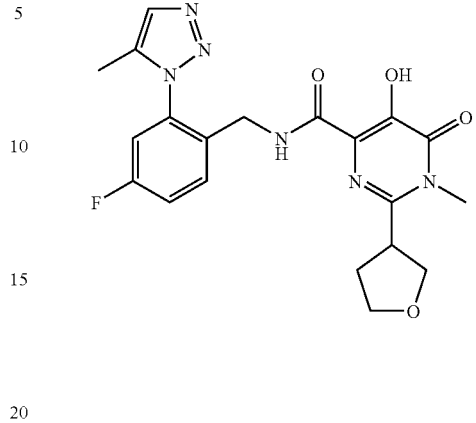

N-(4-fluoro-2-(5-methyl-1H-1,2,3-triazol-1-yl)benzyl)-5-hydroxy-1-methyl-6-oxo-2-(tetrahydrofuran-3-yl)-1,6-dihydropyrimidine-4-carboxamide. White solid (59% yield). $^1$H NMR (500 MHz, CDCl$_3$) δ: 11.87 (s, 1H), 8.44 (brs, 1H), 7.70 (dd, 1H, J=8.55,5.8 Hz), 7.66 (s, 1H), 7.2-7.29 (m, 1H), 7.00 (dd, 1H, J=8.24, 2.44 Hz), 4.27-4.31 (m, 1H), 4.11-4.21 (m, 3H), 4.03-4.06 (m, 1H), 3.95-4.01 (m, 1H), 3.58 (s, 3H), 3.49-3.55 (m, 1H), 2.48-2.53 (m, 1H), 2.30 (s, 3H), 2.28-2.35 (m, 1H). LCMS (M+H)+=429.40. Anal calcd for C$_{21}$H$_{27}$FN$_4$O$_6$S 0.5 H$_2$O: C, 55.87; H, 5.36; N, 18.62; found: C, 56.18; H, 5.77; N, 18.27.

Example 6

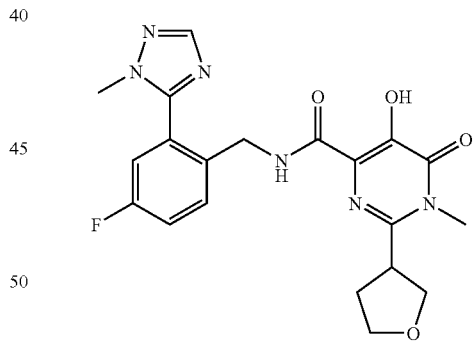

N-(4-fluoro-2-(1-methyl-1H-1,2,4-triazol-5-yl)benzyl)-5-hydroxy-1-methyl-6-oxo-2-(tetrahydrofuran-3-yl)-1,6-dihydropyrimidine-4-carboxamide. White solid (70% yield). $^1$H NMR (500 MHz, CDCl$_3$) δ: 12.03 (brs, 1H), 9.46 (brs, 1H), 8.07 (s, 1H), 7.66 (dd, 1H, J=8.55,5.5 Hz), 7.20-7.24 (m, 1H), 7.11 (dd, 1H, J=8.7, 2.6 Hz), 4.44-4.48 (m, 1H), 4.34-4.38 (m, 1H), 4.28 (dd, 1H, J=8.5, 61 Hz), 4.14 (t, 1H, J=8.09 Hz), 3.97 (s, 3H), 3.92-3.95 (m, 1H), 3.59 (s, 3H), 3.49-3.54 (m, 1H), 2.30-2.38 (m, 2H). LCMS (M+H)+=429.40. Anal calcd for C$_{21}$H$_{27}$FN$_4$O$_6$S 0.5 H$_2$O: C, 55.87; H, 5.36; N, 18.62; found: C, 56.18; H, 5.77; N, 18.27.

Example 7

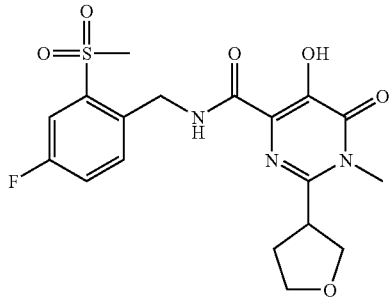

N-(4-fluoro-2-(methylsulfonyl)benzyl)-5-hydroxy-1-methyl-6-oxo-2-(tetrahydrofuran-3-yl)-1,6-dihydropyrimidine-4-carboxamide. White solid (70% yield). $^1$H NMR (500 MHz, CDCl$_3$) δ: 11.78 (s, 1H), 8.59 (brs, 1H), 7.74 (dd, 1H, J=8.24, 2.75 Hz), 7.70 (dd, 1H, J=8.54, 5.19 Hz), 7.32-7.36 (m, 1H), 4.81 (d, 2H, J=6.71), 4.09-4.13 (m, 1H), 4.02-4.06 (m, 1H), 3.92-3.99 (m, 2H), 3.57 (s, 3H), 3.45-3.52 (m, 1H), 3.18 (s, 3H), 2.34-2.40 (m, 1H), 2.25-2.30 (m, 1H). LCMS (M+H)+=426.36. Anal calcd for C$_{18}$H$_{20}$FN$_3$O$_6$S 0.1 TFA: C, 50.04; H, 4.64; N, 9.62; found: C, 49.89; H, 4.35; N, 9.62.

Example 8

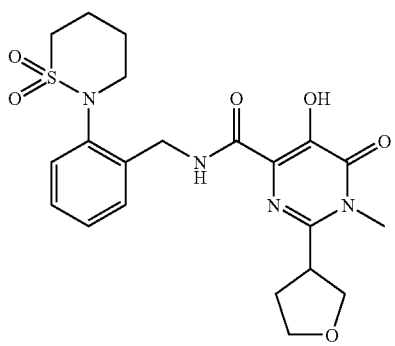

N-(2-(1,1-dioxo-1λ$^6$-[1,2]thiazinan-2-yl)benzylcarbamoyl)-5-hydroxy-1-methyl-6-oxo-2-(tetrahydrofuran-3-yl)-1,6-dihydropyrimidine-4-carboxamide. White solid (35% yield). $^1$H NMR (500 MHz, CDCl$_3$) δ: 12.21 (s, 1H), 8.24-8.28 (m, 1H), 7.43-7.50 (m, 2H), 7.33-7.38 (m, 2H), 4.93-5.0 (m, 1H), 4.42-4.48 (m, 1H), 4.05 (d, 1H, J=6.71), 3.84-3.99 (m, 4H), 3.57 (s, 3H), 3.41-3.48 (m, 2H), 3.20-3.9 (m, 2H), 2.18-2.42 (m, 4H), 1.91-1.98 (m, 2H). LCMS (M+H)+=463.44. Anal calcd for C$_{21}$H$_{26}$N$_4$O$_6$S 0.25 H$_2$O: C, 54.01; H, 5.72; N, 12.00; found: C, 53.68; H, 5.39; N, 11.79.

Example 9

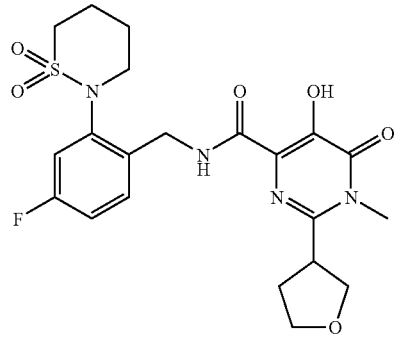

N-(4-fluoro-2-(1,1-dioxo-1λ$^6$-[1,2]thiazinan-2-yl)benzylcarbamoyl)-5-hydroxy-1-methyl-6-oxo-2-(tetrahydrofuran-3-yl)-1,6-dihydropyrimidine-4-carboxamide. White solid (51% yield). $^1$HNMR (500 MHz, CDCl$_3$) δ: 12.15 (s, 1H), 8.24-8.26 (m, 1H), 7.46-7.50 (m, 1H), 7.15-7.18 (m, 1H), 7.05-7.09 (m, 1H), 4.91-4.97 (m, 1H), 4.35-4.41 (m, 1H), 4.05-4.07 (dd, 1H, J=6.87, 2.9), 3.82-3.98 (m, 4H), 3.57 (s, 3H), 3.40-3.49 (m, 2H), 3.22-3.30 (m, 2H), 2.35-2.41 (m, 3H), 2.24-2.28 (m, 1H), 1.91-1.99 (m, 2H). LCMS (M+H)+= 481.47. Anal calcd for C$_{21}$H$_{25}$FN$_4$O$_6$S 0.1 TFA: C, 51.76; H, 5.14; N, 11.39; found: C, 51.72; H, 5.79; N, 11.41.

Example 10

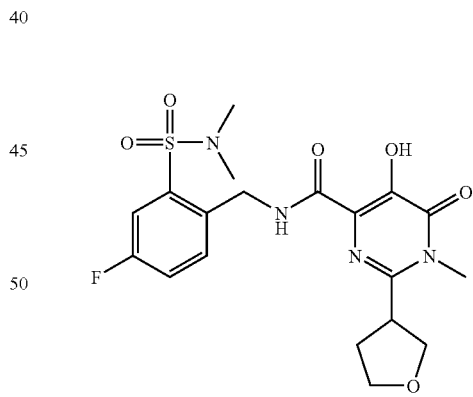

N-(2-(N,N-dimethylsulfamoyl)-4-fluorobenzyl)-5-hydroxy-1-methyl-6-oxo-2-(tetrahydrofuran-3-yl)-1,6-dihydropyrimidine-4-carboxamide. Light yellow solid (3% yield). $^1$H NMR (500 MHz, CDCl$_3$) δ: 11.89 (brs, 1H), 8.61 (brs, 1H), 7.67-7.69 (m, 1H), 7.49 (dd, 1H, J=8.39, 2.59 Hz), 7.22-7.28 (m, 1H), 4.80 (d, 2H, J=7.02), 4.12-4.15 (m, 1H), 4.01-4.06 (m, 1H), 3.93-3.98 (m, 2H), 3.57 (s, 3H), 3.47-3.50 (m, 1H), 2.91 (s, 6H), 2.39-2.43 (m, 1H), 2.24-2.29 (m, 1H). (M+H)+=455.38.

Example 11

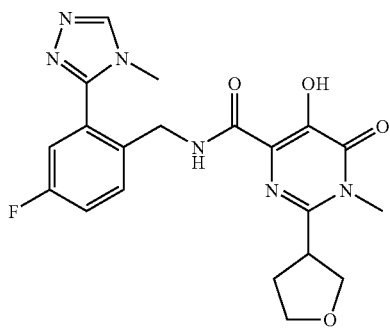

N-(4-fluoro-2-(4-methyl-4H-1,2,4-triazol-3-yl)benzyl)-5-hydroxy-1-methyl-6-oxo-2-(tetrahydrofuran-3-yl)-1,6-dihydropyrimidine-4-carboxamide. Crystaline white solid (68% yield). $^1$H NMR (500 MHz, DMSO-d$_6$) δ: 12.1 (1 H, br. s.), 9.5 (1 H, t, J=6.56 Hz), 8.8 (1 H, s), 7.6 (1 H, dd, J=8.55, 5.80 Hz), 7.5 (1 H, dd, J=9.46, 2.75 Hz), 7.4 (1 H, td, J=8.62, 2.59 Hz), 4.4 (2 H, d, J=6.71 Hz), 4.0-4.0 (2 H, m), 3.9-3.9 (1 H, m), 3.7-3.8 (2 H, m), 3.5 (3 H, s), 2.4-2.5 (1 H, m), 2.1-2.2 (1 H, m). LCMS (M+H)+=529.30. Anal calcd for C$_{20}$H$_{21}$FN$_6$O$_4$ 0.4 H$_2$O, 0.3 EtOH: C, 55.05; H, 5.29; N, 18.70; found: C, 54.65; H, 5.22; N, 18.40.

Example 12

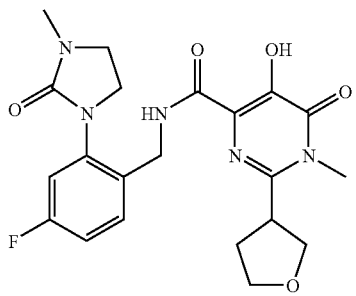

N-(4-fluoro-2-(3-methyl-2-oxoimidazolidin-1-yl)benzyl)-5-hydroxy-1-methyl-6-oxo-2-(tetrahydrofuran-3-yl)-1,6-dihydropyrimidine-4-carboxamide. Off-white solid (48%). $^1$H NMR (500 MHz, CDCl$_3$) δ: 12.30 (s, 1H), 9.10 (brs, 1H), 7.52 (dd, 1H, J=8.7 and 6.56 Hz), 6.93-6.97 (m, 1H), 6.89 (dd, 1H, J=9.77 & 2.75 Hz), 4.51-4.55 (m, 1H), 4.42-4.46 (m, 1H), 4.10-4.17 (m, 2H), 4.02-4.06 (m, 1H), 3.89-3.94 (m, 1H), 3.79-3.82 (m, 2H), 3.57 (s, 3H), 3.55 (t, 2H, J=7.78), 3.43-3.49 (m, 1H), 2.91 (s, 3H), 2.41-2.46 (m, 1H), 2.24-2.29 (m, 1H). LCMS (M+H)+=446.3. Anal calcd for C$_{21}$H$_{24}$FN$_5$O$_5$ 0.55 H$_2$O, 0.1 TFA: C, 54.55; H, 5.44; N, 15.00; found: C, 54.16; H, 5.61; N, 15.11.

Example 13

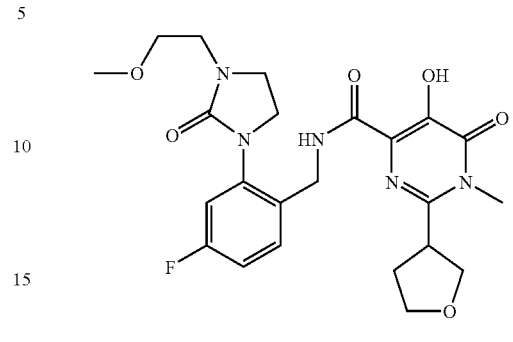

N-(4-fluoro-2-(3-(2-methoxyethyl)-2-oxoimidazolidin-1-yl)benzyl)-5-hydroxy-1-methyl-6-oxo-2-(tetrahydrofuran-3-yl)-1,6-dihydropyrimidine-4-carboxamide. Off-white solid (39%). $^1$H NMR (500 MHz, CDCl$_3$) δ: 12.30 (s, 1H), 9.11 (brs, 1H), 7.53 (dd, 1H, J=8.55 and 6.71 Hz), 6.93-6.97 (m, 1H), 6.90 (dd, 1H, J=9.77 & 2.75 Hz), 4.51-4.55 (m, 1H), 4.42-4.46 (m, 1H), 4.12 (dd, 2H, J=7.02, 3.66 Hz), 3.98-4.02 (m, 1H), 3.87-3.92 (m, 1H), 3.77-3.83 (m, 2H), 3.67 (t, 2H, J=7.63 Hz), 3.55-3.59 (m, 2H), 3.57 (s, 3H), 3.44-3.49 (m, 3H), 3.37 (s, 3H), 2.39-2.45 (m, 1H), 2.20-2.27 (m, 1H). LCMS (M+H)+=490.4. Anal calcd for C$_{23}$H$_{28}$FN$_5$O$_6$ 0.07 H$_2$O, 0.05 TFA: C, 55.89; H, 5.72; N, 14.11; found: C, 55.52; H, 5.32; N, 14.09.

Example 14

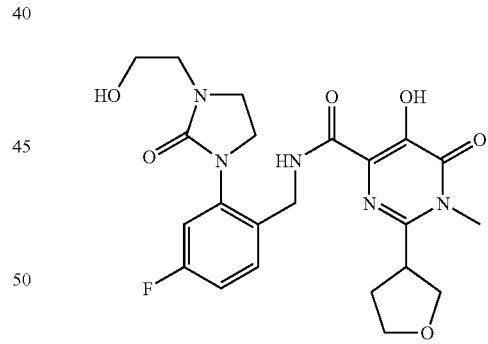

N-(4-fluoro-2-(3-(2-hydroxyethyl)-2-oxoimidazolidin-1-yl)benzyl)-5-hydroxy-1-methyl-6-oxo-2-(tetrahydrofuran-3-yl)-1,6-dihydropyrimidine-4-carboxamide. Light purple solid (3% yield). $^1$H NMR (500 MHz, CDCl$_3$) δ: 12.27 (s, 1H), 9.13 (brs, 1H), 7.57 (dd, 1H, J=8.7 & 6.56 Hz), 6.96-6.99 (m, 1H), 6.90 (dd, 1H, J=9.77 & 2.44 Hz), 4.57-4.63 (m, 2H), 4.40 (dd, 1H, J=8.2&5.5 Hz), 4.01 (q, 2H, J=8.04 Hz), 3.86-3.90 (m, 2H), 3.77-3.82 (m, 3H), 3.69-3.74 (m, 1H), 3.60-3.66 (m, 2H), 3.58 (s, 3H), 3.42-3.49 (m, 1H), 3.32-3.35 (m, 1H), 2.31-2.35 9m, 1H), 2.12-2.18 (m, 1H). (M+H)+=476.1.

Intermediate 5

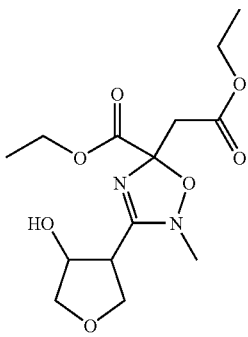

Ethyl 5-(2-ethoxy-2-oxoethyl)-3-(4-hydroxytetrahydrofuran-3-yl)-2-methyl-2,5-dihydro-1,2,4-oxadiazole-5-carboxylate. Intermediate 5 was prepared according to the procedure for intermediate 3 using 4-hydroxytetrahydrofuran-3-carbonitrile (Lin, Y-I; et al EP 0617036 1994 and U.S. Pat. No. 5,602,118; 1997) to afford the desired product as yellow oil (73%). $^1$H NMR (500 MHz, CDCl$_3$) δ: 4.70-4.63 (1H, m), 4.31-4.18 (3H, m), 4.15-4.11 (2H, m), 3.96 (1H, dd, J=9.5, 5.2 Hz), 3.91 (1H, dd, J=9.0, 6.9 Hz), 3.77 (1H, dd, J=9.6, 3.2 Hz), 3.22 (1H, dd, J=16.5, 7.6 Hz), 3.16 (1.5H, s), 3.15 (1.5H, s), 2.95 (1H, dd, J=24.6, 16.5 Hz), 2.94-2.90 (1H, m), 2.39 (1H, dd, J=15.7, 5.7 Hz), 1.31-1.22 (6H, m). HRMS (M+H) calcd for C$_{14}$H$_{23}$N$_2$O$_7$: 331.1505; found: 331.1517.

Intermediate 6

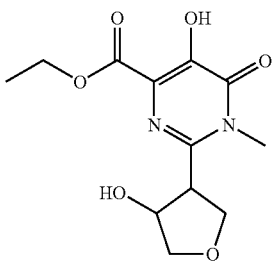

Ethyl 5-hydroxy-2-(4-hydroxytetrahydrofuran-3-yl)-1-methyl-6-oxo-1,6-dihydropyrimidine-4-carboxylate. Intermediate 6 was prepared according to the procedure for intermediate 4 using intermediate 5 to afford the desired product as yellow oil (73%). $^1$H NMR (500 MHz, CDCl$_3$) δ: 1. LCMS (M+H) found: 285.07.

Example 15

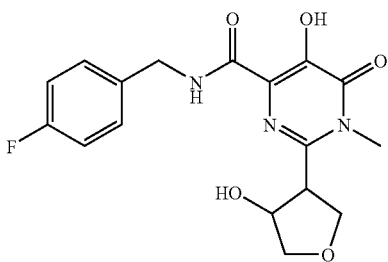

N-(4-Fluorobenzyl)-5-hydroxy-2-(4-hydroxytetrahydrofuran-3-yl)-1-methyl-6-oxo-1,6-dihydropyrimidine-4-carboxamide. The Example 11 was prepared according to the procedure for Example 1 using 4-fluorobenzylamine and intermediate 6 (white solid, 19%). $^1$H NMR (500 MHz, DMSO-d$_6$) δ: 12.28 (1H, s), 9.26-9.19 (1H, m), 7.40-7.36 (2H, m), 7.18 (2H, t, 8.9 Hz), 5.42 (0.25 H, d, J=4.9 Hz), 5.08 (0.75H, d, J=4.9 Hz), 4.70-4.64 (2H, m), 4.50 (2H, d, J=6.4 Hz), 4.17-4.14 (0.25H, m), 4.05-4.02 (0.75H, m), 3.95-3.88 (1H, m), 3.65-3.54 (5H, m). HRMS (M+H) calcd for C$_{17}$H$_{19}$FN$_3$O$_5$: 364.1309; found: 364.1297.

Intermediate 7

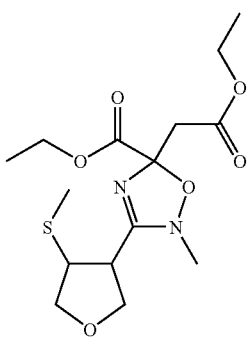

Ethyl 5-(2-ethoxy-2-oxoethyl)-2-methyl-3-(4-(methylthio)tetrahydrofuran-3-yl)-2,5-dihydro-1,2,4-oxadiazole-5-carboxylate. Intermediate 7 was prepared according to the procedure for intermediate 3 using 4-(methylthio)tetrahydrofuran-3-carbonitrile to afford the desired product as pale yellow oil (99%). $^1$H NMR (500 MHz, CDCl$_3$) δ: 4.31-4.10 (6H, m), 3.93-3.88 (1H, m), 3.75-3.62 (2H, m), 3.30-3.21 (1H, m), 3.17 (3H, s), 2.96-2.86 (2H, m), 2.16 (1.5H, s), 2.14 (1.5H, s), 1.32-1.22 (6H, m). HRMS (M+H) calcd for C$_{15}$H$_{25}$N$_2$O$_6$S: 361.1433; found:361.1433. Anal calcd for C$_{21}$H$_{27}$FN$_4$O$_6$S 0.5 H$_2$O: C, H, N, found: C, H, N.

Intermediate 8

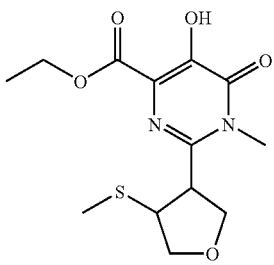

Ethyl 5-hydroxy-1-methyl-2-(4-(methylthio)tetrahydrofuran-3-yl)-6-oxo-1,6-dihydro-pyrimidine-4-carboxylate. Intermediate 8 was prepared according to the procedure for intermediate 4 using intermediate 7 to afford the desired product as pale yellow oil (27%). HRMS (M+H) calcd for C$_{13}$H$_{19}$N$_2$O$_5$S: 315.1015; found: 315.1007.

Example 16

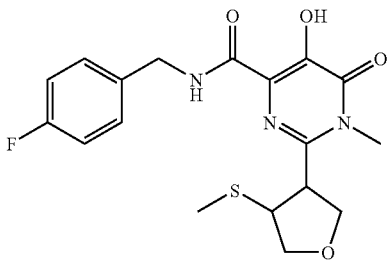

N-(4-Fluorobenzyl)-5-hydroxy-1-methyl-2-(4-(methylthio)tetrahydrofuran-3-yl)-6-oxo-1,6-dihydropyrimidine-4-carboxamide. The Example 12 was prepared according to the procedure for Example 1 using 4-fluorobenzylamine and intermediate 8 in DMF (off-white solid, 49%). $^1$H NMR (500 MHz, CDCl$_3$) δ: 12.05 (1H, s), 7.74 (1H, br s), 7.32-7.29 (2H, m), 7.05 (2H, t, J=8.5 Hz), 4.58 (2H, d, J=6.1 Hz), 4.27-4.23 (2H, m), 3.99 (1H, dd, J=8.5, 6.1 Hz), 3.78 (1H, dd, J=9.2, 6.7 Hz), 3.67-3.63 (1H, m), 3.65 (3H, s), 3.49-3.45 (1H, m), 2.09 (3H, s). HRMS (M+H) calcd for $C_{18}H_{21}FN_3O_4S$: 394.1237; found: 394.1251. Anal calcd for $C_{18}H_{20}FN_3O_4S$: C, 54.95; H, 5.12; N, 10.68; S, 8.15 found: C, 54.66; H, 4.99; N, 10.44; S, 8.05.

Intermediate 9

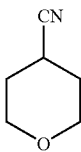

Tetrahydro-2H-pyran-4-carbonitrile. A solution of tetrahydro-4H-pyran-4-one (25 g, 250 mmol) and toluenesulfonylmethyl cyanide (53.7 g, 275 mmol) dissolved in ethylene glycol dimethylether (1 L) was cooled to 0° C. Added dropwise over 30 min was a solution of potassium t-butoxide (56 g, 500 mmol) dissolved in t-butanol (350 mL) and ethylene glycol dimethylether (150 mL). After stirring the resulting mixture for 3 h at room temp, diethyl ether (1 L) was added and the organic phase was washed with saturated aqueous NaHCO$_3$. The organic phase was dried (Na$_2$SO$_4$) and concentrated. The residue was distilled at 39° C. 1.7 mm Hg to give the title compound as colorless oil (10.87 g, 39% yield). $^1$H NMR (300 MHz, CDCl$_3$) δ: 3.91-3.83 (2H, m), 3.61-3.54 (2H, m), 2.89-2.80 (1H, m), 1.97-1.78 (4H, m).

Intermediate 10

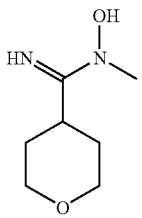

N-Hydroxy-N-methyl-tetrahydro-2H-pyran-4-carboxamidine. To a mixture of tetrahydro-2H-pyran-4-carbonitrile (1.0 g, 9.0 mmol), N-methyl hydroxylamine hydrochloride (1.13 g, 13.5 mmol) in EtOH/H$_2$O (1:1, 20 mL) was added sodium carbonate (0.71 g, 6.75 mmol) and H$_2$O (10 mL) to dissolve. The mixture as stirred at 100° C. for 3 h then cooled and concentrated. The residue was triturated with 10% MeOH/CH$_2$Cl$_2$. The mixture was filtered to give the title compound as a white solid (0.92 g, 65% yield). $^1$H NMR (300 MHz, CDCl$_3$) δ: 4.05 (2H, dd, J=11.2, 3.5 Hz), 3.54 (3H, s), 3.44 (2H, td, J=11.8, 12.3 Hz), 2.48-2.74 (1H, m), 1.83-1.69 (4H, m). LCMS (M+H) calcd for $C_7H_{15}N_2O_2$: 159.11; found: 159.07.

Intermediate 11

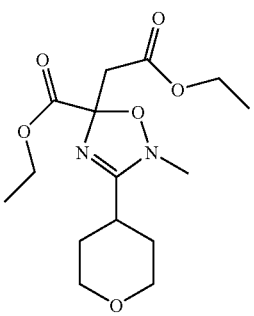

Ethyl 5-(2-ethoxy-2-oxoethyl)-2-methyl-3-(tetrahydro-2H-pyran-4-yl)-2,5-dihydro-1,2,4-oxadiazole-5-carboxylate. To a solution of Compound 8a (0.90 g, 5.8 mmol) dissolved in EtOH (15 mmol) was added diethyl acetylenedicarboxylate (0.1 mL, 6.2 mmol). The resulting mixture was stirred at room temp for 1 h and concentrated. The residue was purified by flash chromatography eluting with 25%-50% EtOAc/hexane to give the title compound as yellow oil (1.22 g, 64% yield). $^1$H NMR (300 MHz, CDCl$_3$) δ: 4.33-4.14 (2H, m), 4.12 (2H, q, J=7.1 Hz), 4.01-3.93 (2H, m), 3.47-3.38 (2H, m), 3.28 (1H, d, J=16.5 Hz), 3.11 (3H, s), 2.90 (1H, d, J=16.5 Hz), 2.48-2.38 (1H, m), 1.92-1.72 (4H, m), 1.27 (3H, t, J=7.1 Hz), 1.22 (3H, t, J=7.12 Hz). LCMS (M+H) calcd for $C_{15}H_{25}N_2O_6$: 329.17; found: 329.33.

Intermediate 12

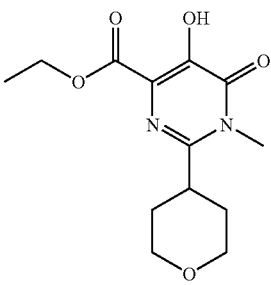

Ethyl 5-hydroxy-1-methyl-6-oxo-2-(tetrahydro-2H-pyran-4-yl-)-1,6-dihydropyrimidine-4-carboxylate. A solution of Compound 8b (1.22 g, 3.7 mmol) in 1,3,5-triisopropylbenzene (30 mL) was stirred at 180° C. for 18 h. The solution was cooled to room temp and was decanted from the residue. Purification by chromatography (YMC Combiprep ODS-A, 30 mm×50 mm, MeOH/H2O/0.1% TFA) gave a solid that was recrystalized from MeOH/H2O to give the title compound as white needles (0.0487 g, 5% yield). $^1$H NMR (300

MHz, CDCl₃) δ: 10.49 (1H, s), 4.41 (2H, q, J=7.2 Hz), 4.10-4.04 (2H, m), 3.60 (3H, s), 3.49 (2H, td, J=11.9, 1.8 Hz), 2.97-2.88 (1H, m), 2.11-1.98 (2H, m), 1.76-1.69 (2H, m), 1.41 (3H, t, J=7.1 Hz). HRMS (M−H) calcd for C₁₃H₁₇N₂O₅: 281.11375; found: 281.1148.

The following Examples were prepared according to the procedure for Example 1 using appropriate benzylamine and intermediate 4 in DMF/EtOH or EtOH as reaction solvent.

Example 17

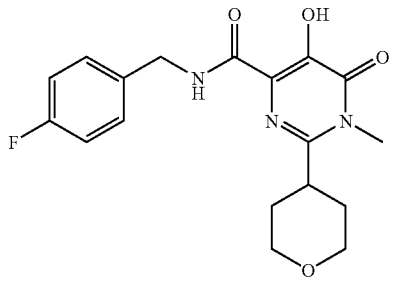

N-(4-Fluorobenzyl)-5-hydroxy-1-methyl-6-oxo-2-(tetrahydro-2H-pyran-4-yl)-1,6-dihydropyrimidine-4-carboxamide. A solution of Compound 8c (0.048 g, 0.17 mmol), 1-methyl-2-pyrrolidinone (2 mL) and 4-fluorobenzylamine (0.11 mL, 0.86 mmol) was stirred at 75° C. for 1.5 h, cooled and purified by chromatography (YMC Combiprep ODS-A, 30 mm×50 mm, MeOH/H2O/0.1% TFA) to give the title compound as a white solid (0.025 g, 41% yield). ¹H NMR (300 MHz, CDCl₃) δ: 11.91 (1H, s), 7.28 (1H, bs), 7.29 (2H, q, J=5.3 Hz), 7.03 (2H, t, J=8.8 Hz), 4.56 (2H, d, J=6.6 Hz), 4.05 (2H, dd, J=11.3, 3.3 Hz), 3.59 (3H, s), 3.47 (2H, td, J=11.9, 1.9 Hz), 2.97-2.87 (1H, m), 1.98-1.84 (2H, m), 1.74-1.69 (2H, m). HRMS (M+H) calcd for C₁₈H₂₁N₃O₄F: 362.15162; found: 362.1518. Anal Calcd for C₁₈H₂₀N₃O₄F/0.05 TFA: C 59.22, H 5.51, N 11.45 F 5.95. Found: C 59.19, H 5.65, N 11.41, F 6.25.

Example 18

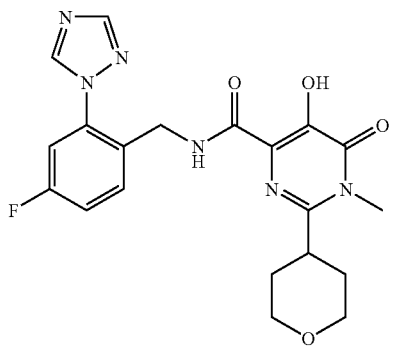

N-(4-fluoro-2-(1H-1,2,4-triazol-1-yl)benzyl)-5-hydroxy-1-methyl-6-oxo-2-(tetrahydro-2H-pyran-4-yl)-1,6-dihydropyrimidine-4-carboxamide. Off-white solid (39% yield). ¹H NMR (500 MHz, DMSO-D6) δ: 11.88 (s, 1H), 9.06 (s, 1H), 8.32 (s, 1H), 7.55-7.59 (m, 2H), 7.41-7.44 (m, 1H), 4.43 (d, 2H, J=6.41 Hz, 3.92 (dd, 2H, J=11.14, 3.51 Hz),3.53 (s, 3H), 3.46 (t, 2H, J=11.75 Hz) 3.10-3.15 (m, 1H), 1.85-1.94 (m, 2H), 1.68-1.72 (m, 2H). LCMS (M+H)+= 429.11. Anal calcd for C₂₀H₂₁FN₆O₄: C, 56.07; H, 4.94; N, 19.61; found: C, 55.97; H, 5.02; N, 19.50.

Example 19

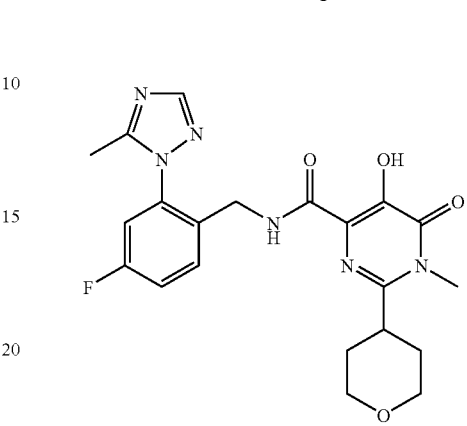

N-(4-fluoro-2-(5-methyl-1H-1,2,4-triazol-1-yl)benzyl)-5-hydroxy-1-methyl-6-oxo-2-(tetrahydro-2H-pyran-4-yl)-1,6-dihydropyrimidine-4-carboxamide. White solid (68% yield). ¹H NMR (500 MHz, DMSO-D6) δ: 11.90 (s, 1H), 9.13 (brs, 1H), 8.09 (s, 1H), 7.55-7.59 (m, 2H), 7.45-7.47 (m, 1H), 4.22 (d, 2H, J=6.41 Hz), 3.92 (dd, 2H, J=11.14, 3.21 Hz),3.53 (s, 3H), 3.46 (t, 2H, J=11.9 Hz), 3.08-3.16 (m, 1H), 2.35 (s, 3H), 1.88-1.97 (m, 2H), 1.71-1.76 (m, 2H). LCMS (M+H)+= 443.2. Anal calcd for C₂₁H₂₇FN₄O₆S 0.5 H₂O: C, 55.87; H, 5.36; N, 18.62; found: C, 56.18; H, 5.77; N, 18.27.

Example 20

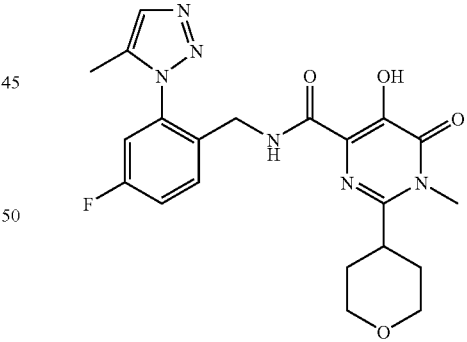

N-(4-fluoro-2-(5-methyl-1H-1,2,3-triazol-1-yl)benzyl)-5-hydroxy-1-methyl-6-oxo-2-(tetrahydro-2H-pyran-4-yl)-1,6-dihydropyrimidine-4-carboxamide. White solid (52% yield). ¹H NMR (500 MHz, DMSO-D6) δ: 11.88 (s, 1H), 9.08 (brs, 1H), 7.74 (s, 1H), 7.59-7.62 (m, 1H), 7.49-7.55 (m, 2H), 4.14 (d, 2H, J=6.41 Hz), 3.92 (dd, 2H, J=11.29, 3.66 Hz), 3.53 (s, 3H), 3.46 (t, 2H, J=11.14 Hz), 3.09-3.14 (m, 1H), 2.32 (s, 3H), 1.88-1.97 (m, 2H), 1.68-1.75 (m, 2H). LCMS (M+H)+= 443.16. Anal calcd for C₂₁H₂₃FN₆O₄: C, 57.00; H, 5.23; N, 18.99; found: C, 56.76; H, 5.34; N, 18.67.

Example 21

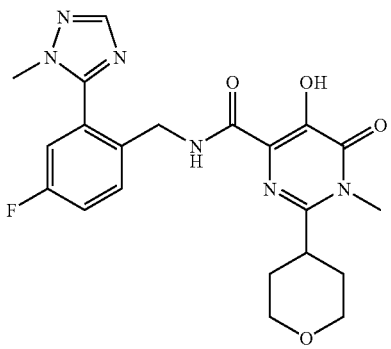

N-(4-fluoro-2-(1-methyl-1H-1,2,4-triazol-5-yl)benzyl)-5-hydroxy-1-methyl-6-oxo-2-(tetrahydro-2H-pyran-4-yl)-1,6-dihydropyrimidine-4-carboxamide. White solid (61% yield). $^1$H NMR (500 MHz, DMSO-D$_6$) δ: 11.96 (brs, 1H), 9.58 (brs, 1H), 8.10 (s, 1H), 7.52-7.62 (m, 2H), 7.40-7.44 (m, 1H), 4.39 (d, 2H, J=6.71 Hz), 3.92 (dd, 2H, J=3.36, 11.29 Hz), 3.87 (s, 3H), 3.53 (s, 3H), 3.48 (t, 1H, 11.29 Hz), 3.18-3.28 (m, 1H), 1.88-1.97 (m, 2H), 1.72-1.79 (m, 2H). LCMS (M+H)+= 443.17. Anal calcd for C$_{21}$H$_{23}$FN$_6$O$_4$: C, 57.00; H, 5.23; N, 18.99; found: C, 56.93; H, 5.34; N, 18.68.

Example 22

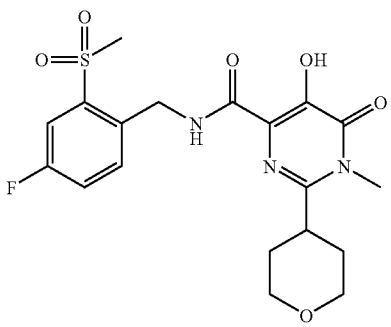

N-(4-fluoro-2-(methylsulfonyl)benzyl)-5-hydroxy-1-methyl-6-oxo-2-(tetrahydro-2H-pyran-4-yl)-1,6-dihydropyrimidine-4-carboxamide. Off-white solid (61% yield). $^1$H NMR (500 MHz, CDCl$_3$) δ: 11.73 (s, 1H), 8.59 (brs, 1H), 7.76 (dd, 1H, J=7.93, 2.75 Hz), 7.70 (dd, 1H, J=8.54, 5.19 Hz), 7.31-7.34 (m, 1H), 4.85 (d, 2H, J=6.71 Hz), 4.09 (dd, 2H, J=11.44, 2.29 Hz), 3.59 (s, 3H), 3.49-3.51 (m, 2H), 3.19 (s, 3H), 2.91-2.94 (m, 1H), 1.97-2.02 (m, 2H), 1.74-1.77 (m, 2H). LCMS (M+H)=440.09. Anal calcd for C$_{19}$H$_{22}$FN$_3$O$_6$S 0.2 TFA: C, 50.05; H, 4.79; N, 8.98; found: C, 49.82; H, 4.70; N, 8.94.

Example 23

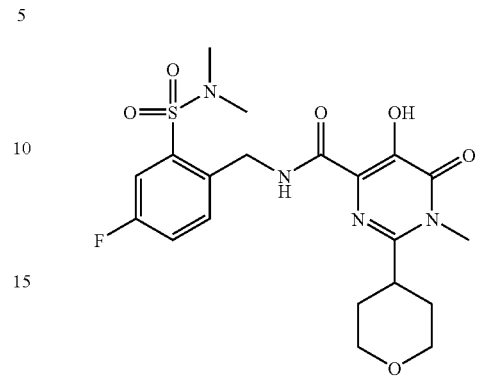

N-(2-(N,N-dimethylsulfamoyl)-4-fluorobenzyl)-5-hydroxy-1-methyl-6-oxo-2-(tetrahydro-2H-pyran-4-yl)-1,6-dihydropyrimidine-4-carboxamide. Off-white solid (60% yield). $^1$H NMR (500 MHz, CDCl$_3$) δ: 11.84 (s, 1H), 8.60 (brs, 1H), 7.68 (dd, 1H, J=8.55, 5.19 Hz), 7.50 (dd, 1H, J=8.55, 2.75 Hz), 7.25-7.29 (m, 1H), 4.82 (d, 2H, J=6.71 Hz), 4.07-4.10 (m, 2H), 3.59 (s, 3H), 3.48-3.51 (m, 2H), 2.91 (s, 6H), 2.28-2.95 (m, 1H), 1.96-2.00 (m, 2H), 1.74-1.77 (m, 2H). LCMS (M+H)=469.26. Anal calcd for C$_{20}$H$_{25}$FN$_4$O$_6$S 0.2 TFA: C, 49.87; H, 5.17; N, 11.40; found: C, 49.59; H, 4.84; N, 11.36.

Example 24

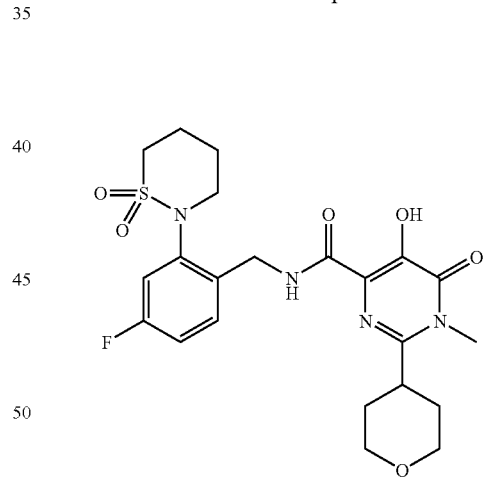

N-(4-fluoro-2-(1,1-dioxo-1λ$^6$-[1,2]thiazinan-2-yl)benzylcarbamoyl)-5-hydroxy-1-methyl-6-oxo-2-(tetrahydro-2H-pyran-4-yl)-1,6-dihydropyrimidine-4-carboxamide. Off-white solid (80% yield). $^1$H NMR (500 MHz, CDCl$_3$) δ: 12.05 (s, 1H), 8.20 (brs, 1H), 7.46 (dd, 1H, J=6.46, 2.44 Hz), 7.17 (dd, 1H, J=9.16, 2.44 Hz), 7.04-7.08 (m, 1H), 4.92 (dd, 1H, J=14.34, 8.54), 4.41 (dd, 1H, J=14.34, 4.27), 4.04 (d, 2H, J=11.6 Hz), 3.82-3.84 (m, 1H), 3.60 (s, 3H), 3.40-3.51 (m, 3H), 3.24-3.30 (m, 2H), 2.87-2.93 (m, 1H), 2.33-2.41 (m, 2H), 1.90-2.05 (m, 4H), 1.68-1.74 (m, 2H). LCMS (M+H)= 495.26. Anal calcd for C$_{22}$H$_{27}$FN$_4$O$_6$S 0.1 TFA: C, 52.70; H, 5.40; N, 11.07; found: C, 52.33; H, 5.17; N, 10.80.

Example 25

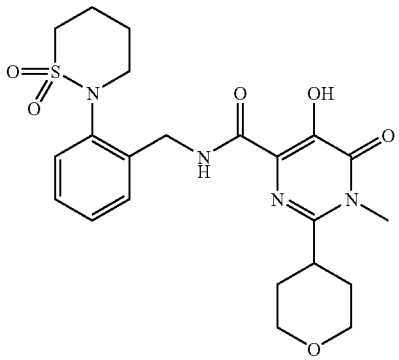

N-(2-(1,1-dioxo-1λ⁶-[1,2]thiazinan-2-yl)benzylcarbamoyl)-5-hydroxy-1-methyl-6-oxo-2-(tetrahydro-2H-pyran-4-yl)-1,6-dihydropyrimidine-4-carboxamide. Off-white solid (11% yield). $^1$H NMR (500 MHz, CDCl$_3$) δ: 12.11 (s, 1H), 8.20 (brs, 1H), 7.45-7.48 (m, 2H), 7.34-7.38 (m, 2H), 4.95 (dd, 1H, J=14.34, 8.24 Hz), 4.48 (dd, 1H, J=14.19, 4.12 Hz), 4.05 (dd, 2H, J=9.61, 1.98 Hz), 3.85-3.90 (m, 1H), 3.60 (s, 3H), 3.41-3.51 (m, 3H), 3.23-3.27 (m, 2H), 2.88-2.92 (m, 1H), 2.34-2.41 (m, 2H), 1.91-1.98 (m, 4H), 1.68-1.74 (m, 2H). LCMS (M+H)+=477.27.

Example 26

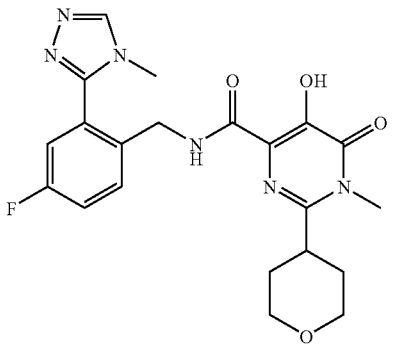

N-(4-fluoro-2-(4-methyl-4H-1,2,4-triazol-3-yl)benzyl)-5-hydroxy-1-methyl-6-oxo-2-(tetrahydro-2H-pyran-4-yl)-1,6-dihydropyrimidine-4-carboxamide. White solid (47%). $^1$H NMR (500 MHz, DMSO-d$_6$) δ: 12.0 (1 H, br. s.), 9.5 (1 H, br. s.), 8.7 (1 H, br. s.), 7.6-7.6 (1 H, m), 7.5-7.5 (1 H, m), 7.4-7.4 (1 H, m), 4.4 (2 H, br. s.), 3.9 (2 H, br. s.), 3.6 (3 H, s), 3.5 (3 H, s), 3.4-3.5 (2 H, m), 3.1-3.1 (1 H, m), 1.9-2.0 (2 H, m), 1.7-1.8 (2 H, m). LCMS (M+H)+=443.35.

We claim:

1. A compound of Formula I

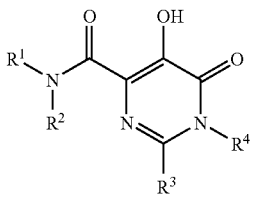

wherein:

$R^1$ is $(Ar^1)$alkyl, $(Ar^1)(CON(R^{10})(R^{11}))$alkyl, $(Ar^1)(CO_2R^{16})$alkyl, $(Ar^1)$hydroxyalkyl, or $(Ar^1)$oxyalkyl;

$R^2$ is hydrogen, alkyl, hydroxy, or alkoxy;

$R^3$ is $C(R^{17})(R^{18})(R^{19})$;

$R^4$ is alkyl;

$R^5$ is hydrogen, halo, hydroxy, cyano, alkyl, cycloalkyl, $C_{5-7}$cycloalkenyl, haloalkyl, alkoxy, alkylthio, haloalkoxy, $N(R^{10})(R^{11})$, $NHAr^2$, $N(R^8)SO_2R^9$, $N(R^8)COR^9$, $N(R^8)CO_2R^9$, $OCOR^9$, $OCO_2R^9$, $OCON(R^{10})(R^{11})$, $OCH_2CO_2R^9$, $OCH_2CON(R^{10})(R^{11})$, $COR^8$, $CO_2R^8$, $CON(R^{10})(R^{11})$, $SOR^9$, $S(=N)R^9$, $SO_2R^9$, $SO_2N(R^8)(R^8)$, $PO(OR^8)_2$, $C_{2-4}(R^{14})$alkynyl, $R^{15}$, $Ar^2$, or $Ar^3$;

$R^6$ is hydrogen, halo, hydroxy, cyano, alkyl, alkoxy, haloalkyl, haloalkoxy, or $N(R^8)(R^8)$;

$R^7$ is hydrogen, halo, hydroxy, cyano, alkyl, alkoxy, haloalkyl, haloalkoxy, or $N(R^8)(R^8)$;

$R^8$ is hydrogen, alkyl, or cycloalkyl;

$R^9$ is alkyl or cycloalkyl;

$R^{10}$ is hydrogen, alkyl, hydroxyalkyl, alkoxyalkyl or dialkylaminoalkyl;

$R^{11}$ is hydrogen, alkyl, hydroxyalkyl, alkoxyalkyl or dialkylaminoalkyl; or $N(R^{10})(R^{11})$ taken together is azetidinyl, pyrrolidinyl, $(R^{12})$-piperidinyl, N—$(R^{13})$-piperazinyl, morpholinyl, thiomorpholinyl, or dioxothiazinyl;

$R^{12}$ is hydrogen, alkyl, or hydroxyalkyl;

$R^{13}$ is hydrogen, alkyl, cyclolkyl, $COR^8$, or $CO_2R^8$;

$R^{14}$ is hydrogen, hydroxy, $N(R^8)(R^8)$, $SO_2R^9$, $OSO_2R^9$, or dioxothiazinyl;

$R^{15}$ is azetidinonyl, pyrrolidinonyl, valerolactamyl, caprolactamyl, maleimido, imidazolidinonyl, oxazolidonyl, or dioxothiazinyl, and is substituted with 0-1 substituents selected from the group consisting of alkyl, alkoxyalkyl, hydroxyalkyl, acetoxyalkyl, and aminoalkyl;

$R^{16}$ is independently hydrogen or alkyl;

or two $R^{16}$'s taken together are $CH_2CH_2$, $CH_2CH_2CH_2$, $CH_2CH_2CH_2CH_2$, $CH_2CH_2CH_2CH_2CH_2$, $CH_2CH_2CH_2CH_2CH_2CH_2$, $OCH_2CH_2$, $CH_2OCH_2$, $OCH_2CH_2CH_2$, $CH_2OCH_2CH_2$, $OCH_2CH_2CH_2CH_2$, $CH_2OCH_2CH_2CH_2$, $CH_2CH_2OCH_2CH_2$, $OCH_2CH_2CH_2CH_2CH_2$, $CH_2OCH_2CH_2CH_2CH_2$, $CH_2CH_2OCH_2CH_2CH_2$, $N(R^8)CH_2CH_2$, $CH_2N(R^8)CH_2$, $N(R^8)CH_2CH_2CH_2$, $CH_2N(R^8)CH_2CH_2$, $N(R^8)CH_2CH_2CH_2CH_2$, $CH_2N(R^8)CH_2CH_2CH_2$, or $CH_2CH_2N(R^8)CH_2CH_2CH_2$, provided that the two $R^{16}$'s are attached to a common carbon atom;

$R^{17}$ and $R^{18}$ taken together with the carbon to which they are attached is a 4-7-membered cyclic ether or a 4-7-membered cyclic thioether, and is substituted with 0-1 substituent selected from the group consisting of hydroxy, alkoxy, alkylthio, alkylSO, alkylSO$_2$, and alkyl;

$R^{19}$ is hydrogen;

$Ar^1$ is

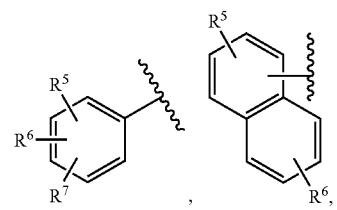

-continued

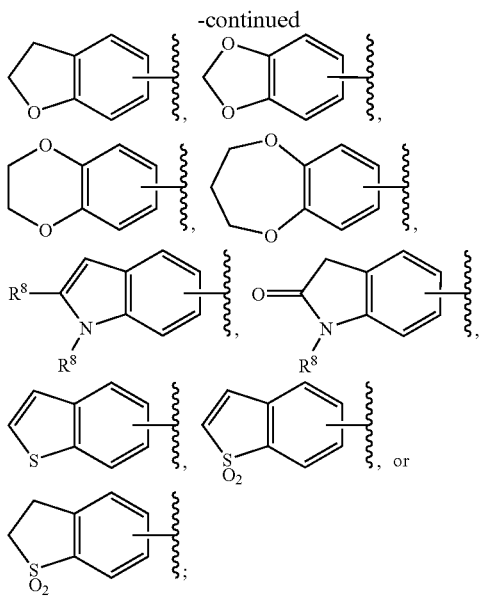

Ar² is tetrazolyl, triazolyl, oxadiazolyl, thiadiazolyl, pyrazolyl, imidazolyl, oxazolyl, thiazolyl, isoxazolyl, isothiazolyl, furanyl, thienyl, pyrrolyl, pyrimidinyl, pyrazinyl, pyridinyl, hydroxypyridinyl, quinolinyl, isoquinolinyl, or indolyl, and is substituted with 0-2 substituents selected from the group consisting of halo, cyano, benzyl, alkyl, alkoxy, $N(R^{10})(R^{11})$, $CON(R^{10})(R^{11})$, $CO_2R^8$, $CONHSO_2N(R^8)(R^8)$, $CONHSO_2N(R^8)$(phenyl), and $CONHSO_2N(R^8)$(halophenyl); and Ar³ is phenyl substituted with 0-2 substituents selected from the group consisting of halo, cyano, hydroxy, alkyl, alkoxy, alkoxymethyl, haloalkyl, haloalkoxy, $N(R^{10})(R^{11})$, $CON(R^8)(R^8)$, and $CH_2N(R^{10})(R^{11})$, or is dioxolanylphenyl; or a pharmaceutically acceptable salt thereof.

2. A compound of claim 1 where $R^{15}$ is azetidinonyl, pyrrolidinonyl, valerolactamyl, caprolactamyl, maleimido, oxazolidonyl, or dioxothiazinyl, and is substituted with 0-1 substituents selected from the group consisting of hydroxymethyl, acetoxymethyl and aminomethyl.

3. A compound of claim 1 where $R^1$ is $(Ar^1)$alkyl.

4. A compound of claim 1 where $R^1$ is

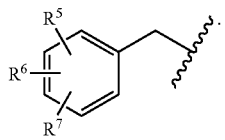

5. A compound of claim 1 where $R^1$ is

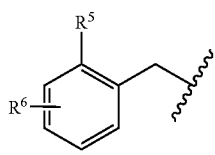

and $R^5$ is other than hydrogen and halo.

6. A compound of claim 1 where $R^1$ is

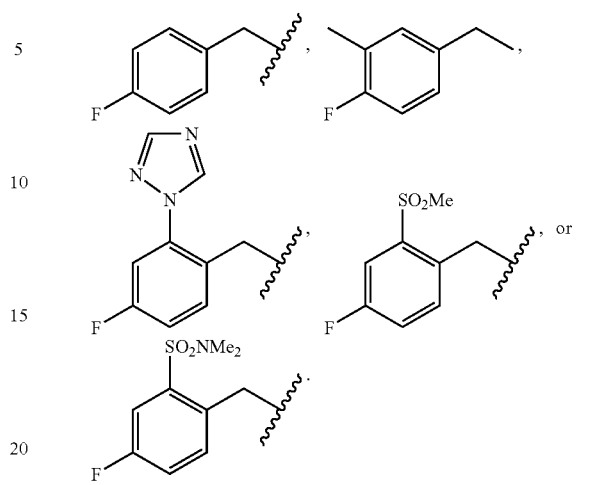

7. A compound of claim 1 where $R^2$ is hydrogen.

8. A compound of claim 1 where $R^3$ is

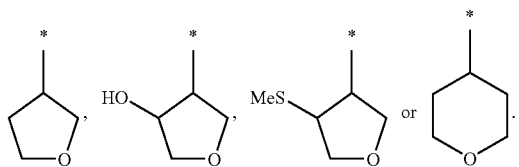

9. A compound of claim 1 where $R^4$ is methyl.

10. A compound of claim 1 where $R^5$ is $R^{15}$.

11. A compound of claim 1 where $R^5$ is tetrazolyl, triazolyl, oxadiazolyl, thiadiazolyl, pyrazolyl, imidazolyl, oxazolyl, thiazolyl, isoxazolyl, isothiazolyl, furanyl, thienyl, or pyrrolyl, and is substituted with 0-2 substituents selected halo and alkyl.

12. A compound of claim 1 selected from the group consisting of

N-(4-Fluorobenzyl)-5-hydroxy-1-methyl-6-oxo-2-(tetrahydrofuran-3-yl)-1,6-dihydropyrimidine-4-carboxamide;

N-(4-Fluoro-3-methylbenzyl)-5-hydroxy-1-methyl-6-oxo-2-(tetrahydrofuran-3-yl)-1,6-dihydropyrimidine-4-carboxamide;

N-(4-fluoro-2-(1H-1,2,4-triazol-1-yl)benzyl)-5-hydroxy-1-methyl-6-oxo-2-(tetrahydrofuran-3-yl)-1,6-dihydropyrimidine-4-carboxamide;

N-(4-fluoro-2-(5-methyl-1H-1,2,4-triazol-1-yl)benzyl)-5-hydroxy-1-methyl-6-oxo-2-(tetrahydrofuran-3-yl)-1,6-dihydropyrimidine-4-carboxamide;

N-(4-fluoro-2-(5-methyl-1H-1,2,3-triazol-1-yl)benzyl)-5-hydroxy-1-methyl-6-oxo-2-(tetrahydrofuran-3-yl)-1,6-dihydropyrimidine-4-carboxamide;

N-(4-fluoro-2-(1-methyl-1H-1,2,4-triazol-5-yl)benzyl)-5-hydroxy-1-methyl-6-oxo-2-(tetrahydrofuran-3-yl)-1,6-dihydropyrimidine-4-carboxamide;

N-(4-fluoro-2-(methylsulfonyl)benzyl)-5-hydroxy-1-methyl-6-oxo-2-(tetrahydrofuran-3-yl)-1,6-dihydropyrimidine-4-carboxamide;

N-(2-(1,1-dioxo-1$\lambda^6$-[1,2]thiazinan-2-yl)benzylcarbamoyl)-5-hydroxy-1-methyl-6-oxo-2--(tetrahydrofuran-3-yl)-1,6-dihydropyrimidine-4-carboxamide;

N-(4-fluoro-2-(1,1-dioxo-1$\lambda^6$-[1,2]thiazinan-2-yl)benzylcarbamoyl)-5-hydroxy-1-methyl-6-oxo-2--(tetrahydrofuran-3-yl)-1,6-dihydropyrimidine-4-carboxamide;

N-(2-(N,N-dimethylsulfamoyl)-4-fluorobenzyl)-5-hydroxy-1-methyl-6-oxo-2-(tetrahydrofuran-3-yl)-1,6-dihydropyrimidine-4-carboxamide;

N-(4-Fluorobenzyl)-5-hydroxy-2-(4-hydroxytetrahydrofuran-3-yl)-1-methyl-6-oxo-1,6--dihydropyrimidine-4-carboxamide;

N-(4-Fluorobenzyl)-5-hydroxy-1-methyl-2-(4-(methylthio)tetrahydrofuran-3-yl)-6-oxo-1,6--dihydropyrimidine-4-carboxamide;

N-(4-Fluorobenzyl)-5-hydroxy-1-methyl-6-oxo-2-(tetrahydro-2H-pyran-4-yl)-1,6-dihydropyrimidine-4-carboxamide;

N-(4-fluoro-2-(1H-1,2,4-triazol-1-yl)benzyl)-5-hydroxy-1-methyl-6-oxo-2-(tetrahydro-2H-pyran-4-yl)-1,6-dihydropyrimidine-4-carboxamide;

N-(4-fluoro-2-(5-methyl-1H-1,2,4-triazol-1-yl)benzyl)-5-hydroxy-1-methyl-6-oxo-2-(tetrahydro-2H-pyran-4-yl)-1,6-dihydropyrimidine-4-carboxamide;

N-(4-fluoro-2-(5-methyl-1H-1,2,3-triazol-1-yl)benzyl)-5-hydroxy-1-methyl-6-oxo-2-(tetrahydro-2H-pyran-4-yl)-1,6-dihydropyrimidine-4-carboxamide;

N-(4-fluoro-2-(1-methyl-1H-1,2,4-triazol-5-yl)benzyl)-5-hydroxy-1-methyl-6-oxo-2-(tetrahydro-2H-pyran-4-yl)-1,6-dihydropyrimidine-4-carboxamide;

N-(4-fluoro-2-(methylsulfonyl)benzyl)-5-hydroxy-1-methyl-6-oxo-2-(tetrahydro-2H-pyran-4-yl)-1,6-dihydropyrimidine-4-carboxamide;

N-(2-(N,N-dimethylsulfamoyl)-4-fluorobenzyl)-5-hydroxy-1-methyl-6-oxo-2-(tetrahydro-2H-pyran-4-yl)-1,6-dihydropyrimidine-4-carboxamide;

N-(4-fluoro-2-(1,1-dioxo-1$\lambda^6$-[1,2]thiazinan-2-yl)benzylcarbamoyl)-5-hydroxy-1-methyl-6-oxo-2-(tetrahydro-2H-pyran-4-yl)-1,6-dihydropyrimidine-4-carboxamide; and N-(2-(1,1-dioxo-1$\lambda^6$-[1,2]thiazinan-2-yl)benzylcarbamoyl)-5-hydroxy-1-methyl-6-oxo-2-(tetrahydro-2H-pyran-4-yl)-1,6-dihydropyrimidine-4-carboxamide;

or a pharmaceutically acceptable salt thereof.

13. A compound of claim 1 selected from the group consisting of

N-(4-fluoro-2-(4-methyl-4H-1,2,4-triazol-3-yl)benzyl)-5-hydroxy-1-methyl-6-oxo-2-(tetrahydrofuran-3-yl)-1,6-dihydropyrimidine-4-carboxamide;

N-(4-fluoro-2-(3-methyl-2-oxoimidazolidin-1-yl)benzyl)-5-hydroxy-1-methyl-6-oxo-2-(tetrahydrofuran-3-yl)-1,6-dihydropyrimidine-4-carboxamide;

N-(4-fluoro-2-(3-(2-methoxyethyl)-2-oxoimidazolidin-1-yl)benzyl)-5-hydroxy-1-methyl-6-oxo-2-(tetrahydrofuran-3-yl)-1,6-dihydropyrimidine-4-carboxamide;

N-(4-fluoro-2-(3-(2-hydroxyethyl)-2-oxoimidazolidin-1-yl)benzyl)-5-hydroxy-1-methyl-6-oxo-2-(tetrahydrofuran-3-yl)-1,6-dihydropyrimidine-4-carboxamide; and N-(4-fluoro-2-(4-methyl-4H-1,2,4-triazol-3-yl)benzyl)-5-hydroxy-1-methyl-6-oxo-2-(tetrahydro-2H-pyran-4-yl)-1,6-dihydropyrimidine-4-carboxamide;

or a pharmaceutically acceptable salt thereof.

14. A composition useful for treating HIV infections comprising a therapeutic amount of a compound of claim 1 and a pharmaceutically acceptable carrier.

15. The composition of claim 14 further comprising a therapeutically effective amount at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

16. A method for treating HIV-1 infection comprising administering a therapeutically effective amount of a compound of claim 1, or a pharmaceutically acceptable salt thereof, to a patient in need thereof.

17. The method of claim 16 further comprising administering a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

* * * * *

UNITED STATES PATENT AND TRADEMARK OFFICE
CERTIFICATE OF CORRECTION

PATENT NO. : 7,763,630 B2 Page 1 of 1
APPLICATION NO. : 12/132145
DATED : July 27, 2010
INVENTOR(S) : B. Narasimhulu Naidu et al.

It is certified that error appears in the above-identified patent and that said Letters Patent is hereby corrected as shown below:

In the Specification:

Column 3, line 19, change "cyclolkyl" to -- cycloalkyl --.

In the Claims:

Claim 1:
Column 36, line 28, change "cyclolkyl" to -- cycloalkyl --.
Column 36, line 46, after "N(R$^8$)CH$_2$CH$_2$CH$_2$CH$_2$," insert -- CH$_2$N(R$^8$)CH$_2$CH$_2$CH$_2$, CH$_2$CH$_2$N(R$^8$)CH$_2$CH$_2$, N(R$^8$)CH$_2$CH$_2$CH$_2$CH$_2$CH$_2$, --.

Claim 12:
Column 39, line 2, change "2--(tetrahydrofuran" to -- 2-(tetrahydrofuran --.
Column 39, lines 5 and 6, change "2--(tetrahydrofuran" to -- 2-(tetrahydrofuran --.
Column 39, line 11, change "1,6--dihydropyrimidine" to -- 1,6-dihydropyrimidine --.
Column 39, lines 14 and 15, change "1,6--dihydropyrimidine" to -- 1,6-dihydropyrimidine --.

Claim 14:
Column 40, line 19, change "HIV" to -- HIV-1 --.

Signed and Sealed this
Twelfth Day of February, 2013

Teresa Stanek Rea
*Acting Director of the United States Patent and Trademark Office*